US012709610B2

(12) United States Patent
Liu et al.

(10) Patent No.: US 12,709,610 B2
(45) Date of Patent: Aug. 18, 2026

(54) PREPARATION METHOD FOR HEPATITIS B VIRUS NUCLEOCAPSID INHIBITOR

(71) Applicant: Shanghai Zhimeng Biopharma, Inc., Shanghai (CN)

(72) Inventors: Gang Liu, Shanghai (CN); Bo Liang, Shanghai (CN); Huanming Chen, Shanghai (CN); Zhaojian Jiang, Pudong New Area Shanghai (CN)

(73) Assignee: SHANGHAI ZHIMENG BIOPHARMA, INC., Shanghai (CN)

( * ) Notice: Subject to any disclaimer, the term of this patent is extended or adjusted under 35 U.S.C. 154(b) by 371 days.

(21) Appl. No.: 18/291,212

(22) PCT Filed: Jul. 22, 2022

(86) PCT No.: PCT/CN2022/107463
§ 371 (c)(1),
(2) Date: Jan. 22, 2024

(87) PCT Pub. No.: WO2023/001298
PCT Pub. Date: Jan. 26, 2023

(65) Prior Publication Data

US 2024/0336607 A1 Oct. 10, 2024

(30) Foreign Application Priority Data

Jul. 23, 2021 (CN) ......................... 202110839582.2

(51) Int. Cl.
*C07D 413/14* (2006.01)
*A61K 31/422* (2006.01)

(52) U.S. Cl.
CPC .......... *C07D 413/14* (2013.01); *A61K 31/422* (2013.01)

(58) Field of Classification Search
None
See application file for complete search history.

(56) References Cited

U.S. PATENT DOCUMENTS

2017/0107234 A1 4/2017 Kawasuji et al.
2019/0152963 A1 5/2019 Chen

FOREIGN PATENT DOCUMENTS

CN 102532042 A 7/2012
CN 106928098 A 7/2017
CN 109311865 A 2/2019

OTHER PUBLICATIONS

Kumata et al., "One-pot radiosynthesis of [13N]urea and [13N]carbamate using no-carrier-added [13N]NH3," Journal of Labelled Compounds and Radiopharmaceuticals, vol. 52, pp. 166-172 (2009).

Office Action issued on Jan. 21, 2025, in RU Application No. 2024104564.

Sanabria et al., "Efficient Direct Halogenation of Unsymmetrical N-Benzyl- and N-Phenylureas with Trihaloisocyanuric Acids," Synthesis, vol. 50, pp. 1359-1367 (2018).

Barbero, N. et al., "Copper-catalyzed intramolecular N-arylation of ureas in water: a novel entry to benzoimidazolones," Tetrahedron, vol. 64, pp. 7283-7288 (2008).

Hatton, W. et al., "Synthesis of non glycosidic nucleobase-sugar mimetics," Comptes Rendus Chimie, vol. 13, No. 10, pp. 1284-1300 (2010).

Mclaughlin, M. et al., "Efficient Access to Cyclic Ureas via Pd-Catalyzed Cyclization," Organic Letters pp. 3311-3314, vol. 8, No. 15 (2006).

International Search Report and Written Opinion issued Aug. 29, 2022 in PCT/CN2022/107463 (Translation of ISR only).

*Primary Examiner* — Kamal A Saeed
*Assistant Examiner* — Quincy McKoy
(74) *Attorney, Agent, or Firm* — Panitch Schwarze Belisario & Nadel LLP

(57) ABSTRACT

A method for preparing a hepatitis B virus nucleocapsid inhibitor is provided. Specifically, the method involves a novel procedure for preparing a compound represented by formula (I) (each group is as defined in the description) by an optimization process. The method can significantly enhance the yield, improve the product purity, and significantly reduce genotoxic impurities in the product. Also disclosed is a new intermediate for the preparation of the compound represented by formula (I).

I

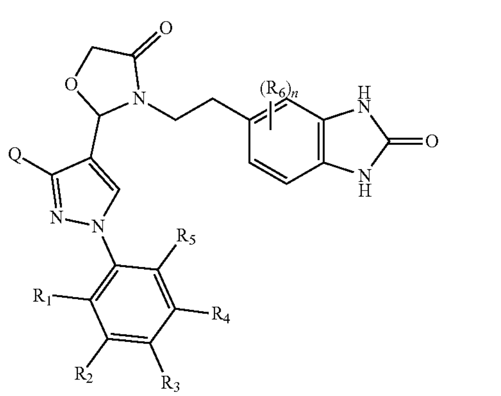

10 Claims, No Drawings

PREPARATION METHOD FOR HEPATITIS B VIRUS NUCLEOCAPSID INHIBITOR

CROSS-REFERENCE TO RELATED APPLICATIONS

This application is a Section 371 of International Application No. PCT/CN2022/107463, filed Jul. 22, 2022, which was published in the Chinese language on Jan. 26, 2023 under International Publication No. WO 2023/001298 A1, which claims priority under 35 U.S.C. § 119(b) to Chinese Application No. 202110839582.2, filed Jul. 23, 2021, the disclosures of which are incorporated herein by reference in their entireties.

TECHNICAL FIELD

The present invention relates to the field of medicine and fine chemical, and specifically relates to a preparation method for hepatitis B virus nucleocapsid inhibitor and new intermediates for the preparation of the inhibitor.

BACKGROUND

I

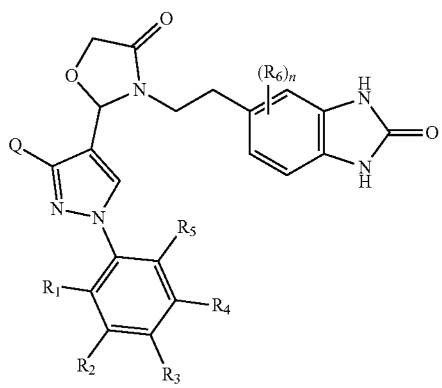

The compounds represented by formula I are hepatitis B virus nucleocapsid inhibitors, developed by Shanghai Zhimeng Biopharma, INC. and are a new class of drugs for viral hepatitis B in the clinical trial stage. Currently marketed hepatitis B drugs can control the replication of hepatitis B virus in a limited way and slow down the progression of cirrhosis, but can rarely achieve the goal of curing chronic hepatitis B. The compounds of Formula I improve the functional cure rate of chronic hepatitis B by inhibiting nucleocapsid formation of HBV virus, and the results of preclinical studies have shown that they have excellent safety and efficacy.

Therefore, the development and optimization of the preparation process of the above compounds are of great significance to reduce their production cost, promote their marketization and benefit more patients at an early date.

SUMMARY OF INVENTION

The purpose of the present invention is to provide a method for preparing a compound of formula I with high yield, mild conditions, high purity of the product, low side reactions, and ease of operation, and without the use of intermediates having genotoxicity.

A further purpose of the present invention is to provide new intermediates for the preparation of the compound of formula I, i.e., the compound of formula II and the compound of formula III.

In a first aspect of the present invention, provided is a preparation method for a compound of formula I, or a pharmaceutically acceptable salt thereof, or a tautomer thereof, or a stereoisomer thereof, or a racemate thereof, comprising steps of:

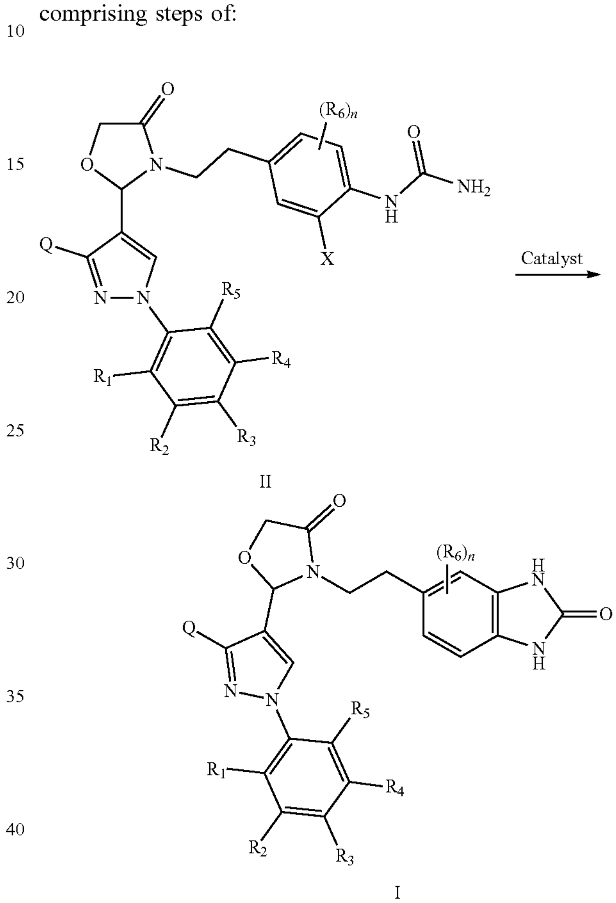

II

I

1) In the presence of a catalyst, subjecting a compound of formula II to cyclization to obtain a compound of formula I;

wherein, $R_1$, $R_2$, $R_3$, $R_4$, and $R_5$ are each independently selected from the group consisting of: hydrogen, deuterium, halogen, substituted or unsubstituted C1-C6 alkyl, amino, hydroxyl and nitro, wherein the "substituted" refers to being substituted by one or more (e. g., 2, 3, 4, or 5) substituents selected from the group consisting of: halogen, nitro, amino, and hydroxyl;

$R_6$ is selected from the group consisting of: hydrogen, deuterium, halogen, amino, and hydroxyl;

n is 0, 1, 2, 3 or 4;

Q is selected from the group consisting of: C6-C10 aryl substituted or unsubstituted by one or more halogens, 6-10-membered heteroaryl containing 1-3 heteroatoms selected from N, O and S and substituted or unsubstituted by one or more halogens;

X is halogen.

In another preferred embodiment, the stereoisomer of formula I is an R isomer.

In another preferred embodiment, the stereoisomer of formula I is an S isomer.

In another preferred embodiment, the R isomer is the structure shown in the following formula I-R:

I-R

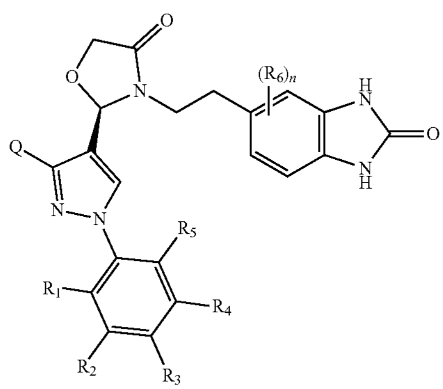

wherein, each group is as defined above.

In another preferred embodiment, $R_1$, $R_2$, $R_3$, $R_4$, and $R_5$ are each independently selected from the group consisting of: hydrogen, deuterium, and halogen.

In another preferred embodiment, n is 0.

In another preferred embodiment, Q is halogen-substituted C6-C10 aryl, preferably halogen-substituted phenyl, or deuterium and halogen co-substituted phenyl.

In another preferred embodiment, X is bromine or iodine.

In another preferred embodiment, in step 1), the catalyst is a substance or hydrate thereof selected from the group consisting of: copper (cuprous) iodide, copper (cuprous) chloride, copper (cuprous) bromide, copper sulphate, copper powder, copper (cuprous) oxide, copper (cuprous) hydroxide, copper (cuprous) acetate, copper citrate, copper methanesulfonate, copper fluoborate, basic copper carbonate, copper gluconate, copper (cuprous) tartrate, copper acetylacetonate, copper 8-hydroxyquinoline, copper (cuprous) thiocyanate, copper (cuprous) nitrate, copper (cuprous) cyanide, copper oxalate, copper phosphate, copper (cuprous) trifluoromethanesulfonate, copper formate, copper selenide, copper dichloro (1,10-phenanthroline), (1,10-phenanthroline) (trifluoromethyl) copper, CuTC, and combinations thereof.

In the present invention, CuTC refers to copper(I) thiophene-2-carboxylate.

In another preferred embodiment, step 1) is carried out in the coexistence of both a catalyst and a ligand selected from the group consisting of:

L1

L2

L3

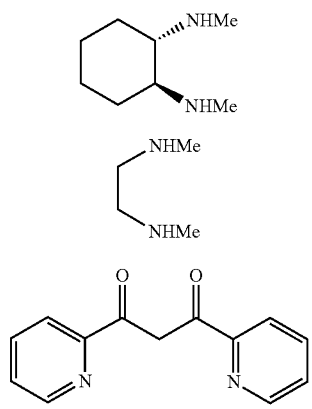

-continued

L4

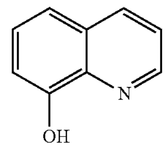

L5

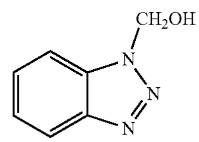

L6

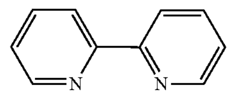

L7

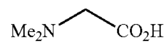

L8

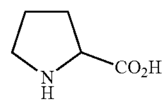

L9

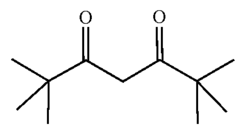

L10

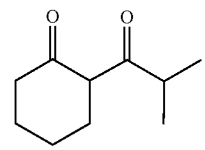

L11

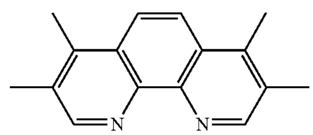

L12

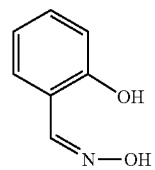

L13

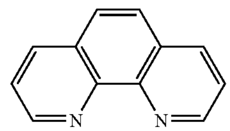

L14

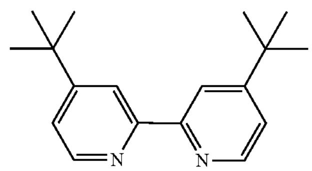

-continued

L15

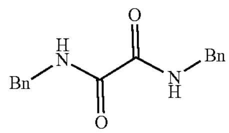

L16

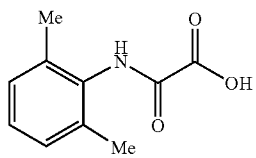

L17

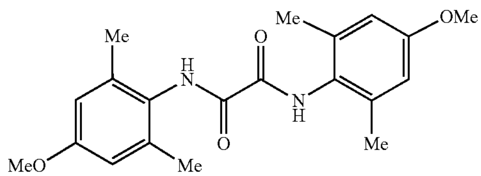

L18

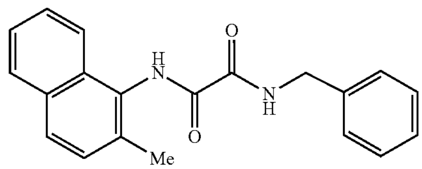

L19

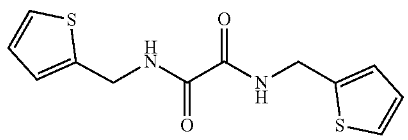

L20

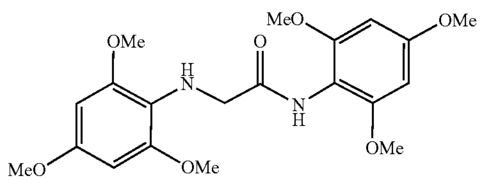

L21

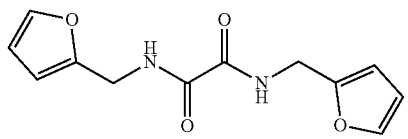

L22

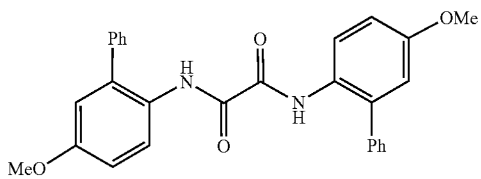

L23

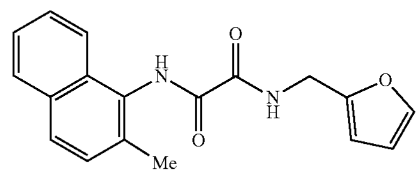

-continued

L24

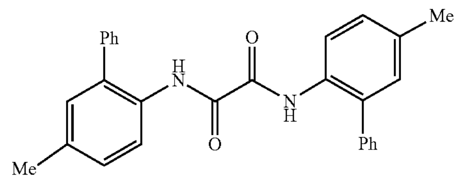

L25

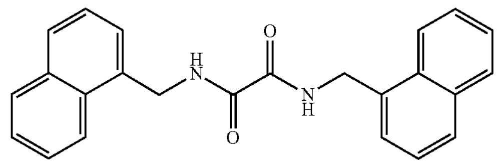

L26

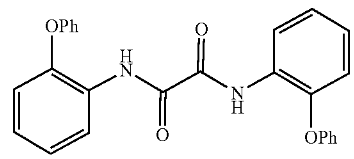

In another preferred embodiment, in step 1), the catalyst is copper powder.

In another preferred embodiment, in step 1), the molar ratio of the catalyst to the compound of formula II is 0.2-3, preferably, 0.4-2, more preferably, 0.6-1.5; most preferably, 0.8-1.2.

In another preferred embodiment, step 1) is carried out at 40-150° C., preferably, 50-130° C., more preferably, 60-110° C.

In another preferred embodiment, the reaction time of step 1) is 0.1-36 h, preferably 0.3-10 h, more preferably 0.4-5 h.

In another preferred embodiment, in step 1), the catalyst is selected from the group consisting of: cuprous oxide, cuprous chloride, cuprous iodide, and combinations thereof.

In another preferred embodiment, step 1) is carried out in the coexistence of both a catalyst and a ligand, with the molar ratio of the catalyst to the compound of formula II being 0.0001-1 (preferably 0.001-0.5, more preferably 0.005-0.2, most preferably 0.01-0.1);

the molar ratio of the catalyst to the ligand is 0.2-5.0 (preferably 0.5-2.0, more preferably 0.8-1.2).

In another preferred embodiment, step 1) is carried out in the presence of a base.

In another preferred embodiment, in step 1), the base is selected from the group consisting of: 1,5-diazabicyclo [5.4.0]-5undecene, 1,8-diazabicyclo[5.4.0]undec-7-ene (DBU), cesium carbonate, sodium carbonate, potassium carbonate, sodium tert-butanolate, potassium tert-butanolate, potassium phosphate, potassium hydroxide, sodium hydroxide, lithium hydroxide, bis(trimethylsilyl)aminolithium, bis(trimethylsilyl)amino potassium, bis(trimethylsilyl)aminosodium, and combinations thereof.

In another preferred embodiment, the molar ratio of the base to the compound of formula II in step 1) is 0.5-5.0, preferably 1.0-2.0.

In another preferred embodiment, the compound I is selected from the group consisting of:

-continued
1
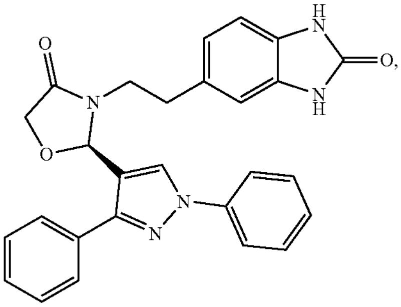
2
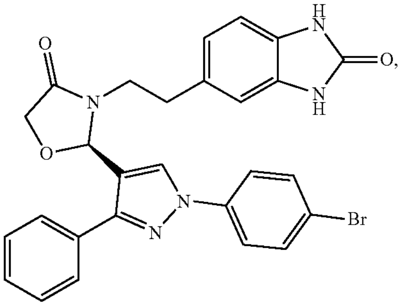
3
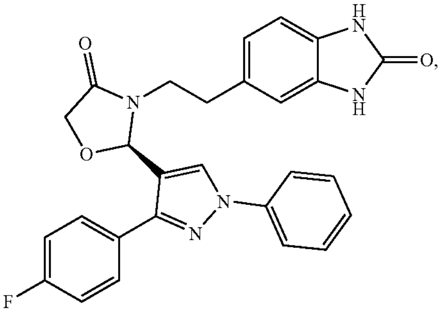
4
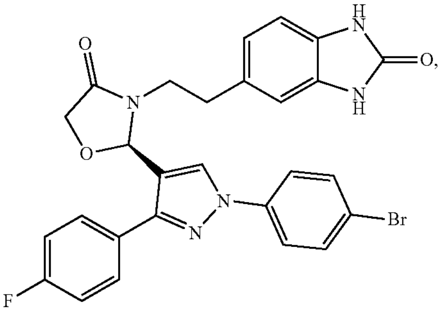
5
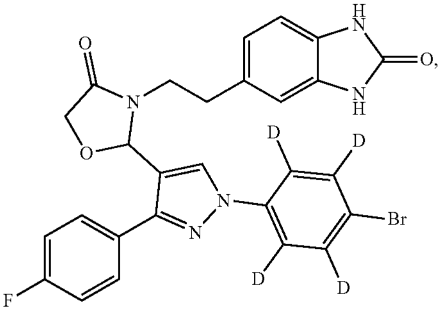
6
7
and
8
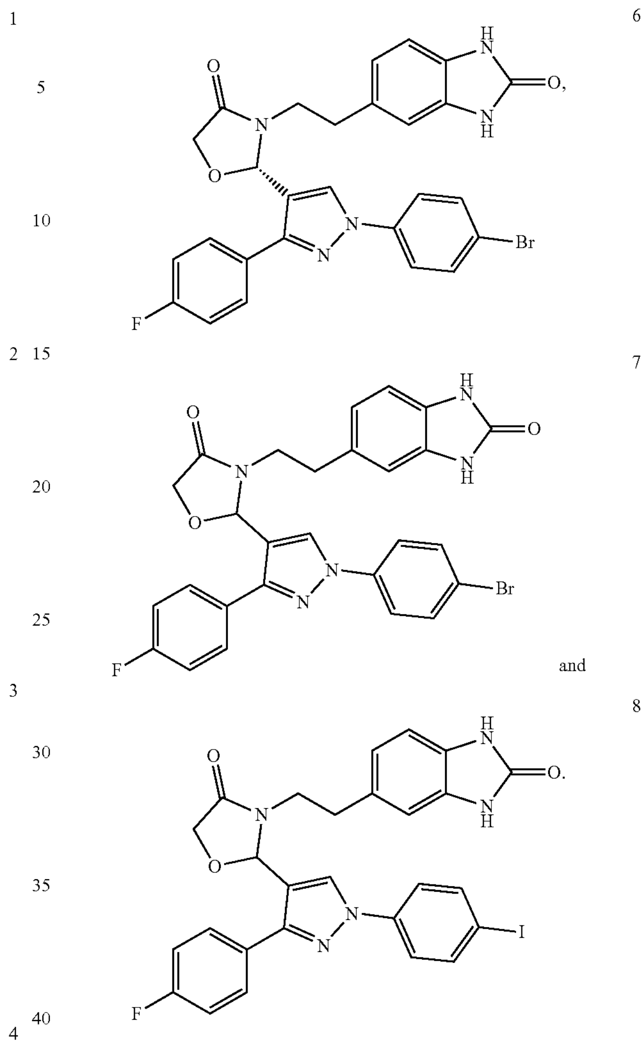
In another preferred embodiment, before step 1), the method further comprises steps of:
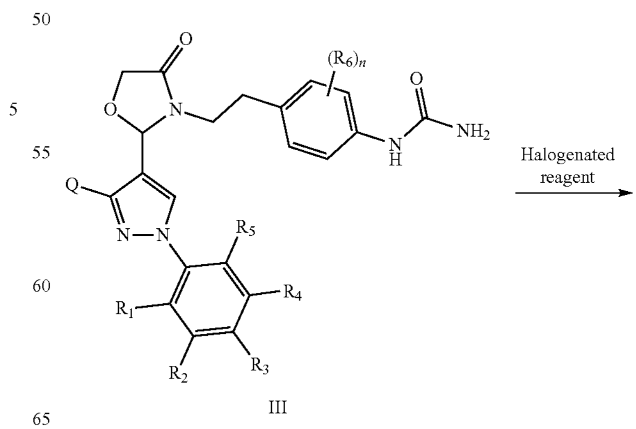
III -continued

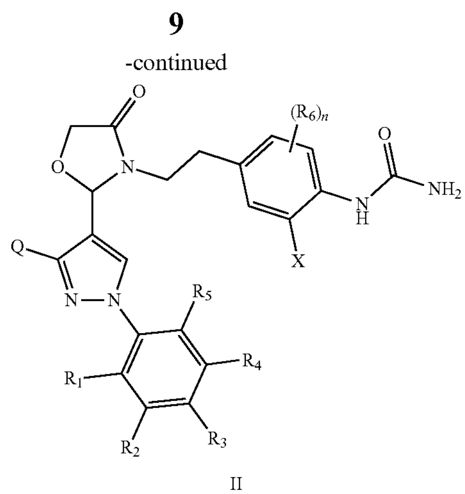

II 2) reacting a compound of formula III with a halogenated reagent to obtain a compound of formula II;

in the compound of formula III, $R_1$, $R_2$, $R_3$, $R_4$, $R_5$, $R_6$, n, X and Q are as defined in claim 1.

In another preferred embodiment, in step 2), the halogenated reagent is selected from the group consisting of: N-iodosuccinimide (NIS), iodine, 1,3-diiodo-5,5-dimethylhydantoin, N-bromosuccinimide, bromine, 1,3-dibromo-5,5-dimethylhydantoin, chlorine, N-chlorosuccinimide, n-bromosuccinimide (NBS), and combinations thereof.

In another preferred embodiment, the molar ratio of the halogenated reagent to the compound of formula III in step 2) is 0.8-2, preferably 0.9-1.8, more preferably 1.1-1.5.

In another preferred embodiment, step 2) is carried out at 40-100° C., preferably 50-90° C., more preferably 55-85° C.

In another preferred embodiment, step 2) is carried out in a solvent selected from the group consisting of: acetonitrile, dimethylformamide, and combinations thereof, preferably acetonitrile.

In another preferred embodiment, before step 2), the preparation method further comprises the following steps:

3) reacting the compound of formula IV with a carbonylation reagent to obtain an isocyanate intermediate of formula IV-1;

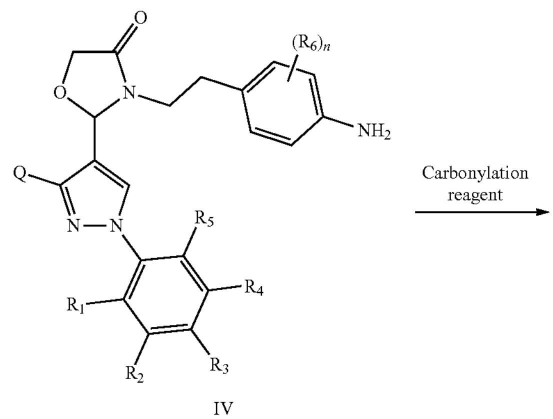

IV

-continued

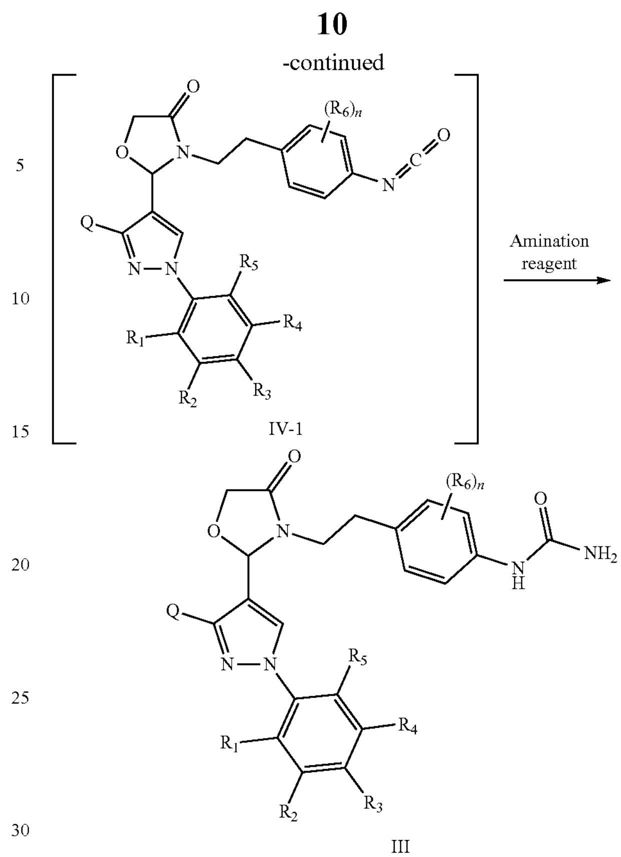

IV-1

III 4) reacting the isocyanate intermediate of formula IV-1 obtained from step 3) without separation with the amination reagent directly in the system to obtain the compound of formula III;

in the compound of formula IV and the isocyanate intermediate of formula IV-1, $R_1$, $R_2$, $R_3$, $R_4$, $R_5$, $R_6$, n and Q are as defined in claim 1.

In another preferred embodiment, the compound of formula IV is an R isomer.

In another preferred embodiment, in step 3), the carbonylation reagent is selected from the group consisting of: triphosgene, CDI, potassium isocyanate, and combinations thereof; and/or in step 4), the amination reagent is selected from the group consisting of: ammonia, ammonia gas, an organic solution of ammonia, and combinations thereof.

In another preferred embodiment, in step 3), the carbonylation reagent is triphosgene.

In another preferred embodiment, in step 3), the molar ratio of the carbonylation reagent to the compound of formula IV is 0.2-2, preferably 0.25-1.5, more preferably 0.3-1.2.

In another preferred embodiment, step 3) and/or step 4) is carried out in the presence of a base selected from the group consisting of: pyridine, triethylamine, imidazole, and combinations thereof.

In another preferred embodiment, in step 3) and/or step 4), the base is pyridine.

In another preferred embodiment, in step 3) and/or step 4), the molar ratio of the base to the compound of formula IV is 0.5-5, preferably 1.0-4.0, more preferably 2.0-3.5.

In another preferred embodiment, the molar ratio of the amination reagent to the compound of formula IV is 1.0-30, preferably 3-20, more preferably 8.0-15.

In another preferred embodiment, step 3) and/or step 4) is carried out in a solvent selected from the group consisting of: tetrahydrofuran, methyltetrahydrofuran, dichloromethane, dioxane, toluene, xylene, ethyl acetate, acetonitrile, ethylene glycol dimethyl ether, and combinations thereof.

In another preferred embodiment, step 3) and/or step 4) is carried out in dichloromethane.

In another preferred embodiment, step 3) is carried out at −40-40° C., preferably −30-30° C., more preferably −20-20° C.

In another preferred embodiment, step 4) is carried out at −40-10° C., preferably −30-5° C., more preferably −20-0° C.

In another preferred embodiment, in step 4), the reaction is quenched with water between 10-40° C.

In a second aspect of the present invention, provided is an intermediate shown in formula II.

II

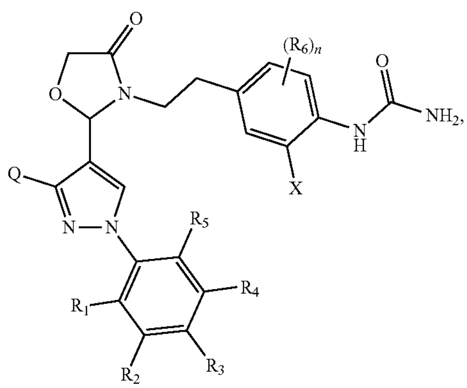

$R_1$, $R_2$, $R_3$, $R_4$, $R_5$, $R_6$, n, X and Q are as defined in the first aspect of the present invention.

In another preferred embodiment, the intermediate shown in formula II is selected from the group consisting of:

9

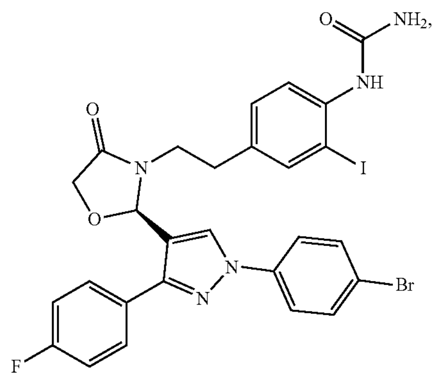

-continued

10

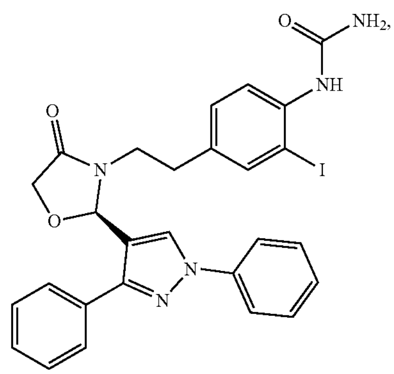

11

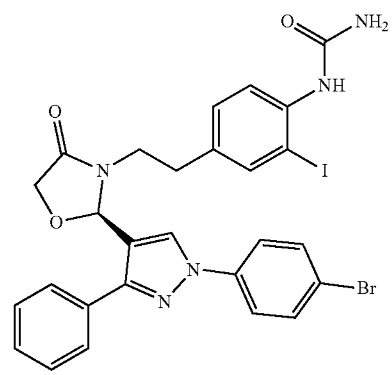

12

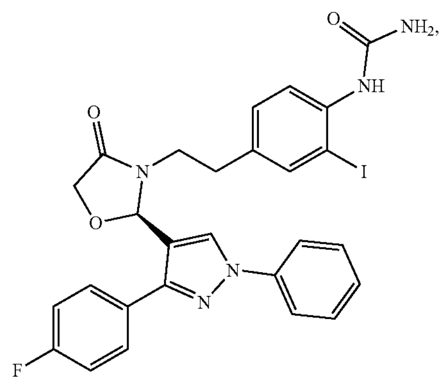

13

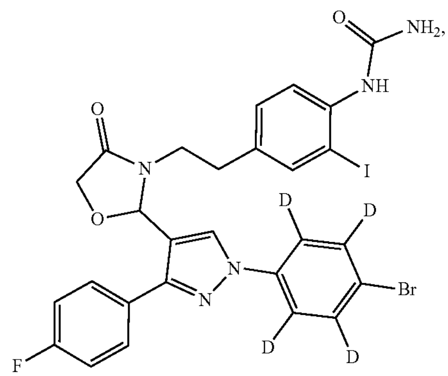

-continued
14
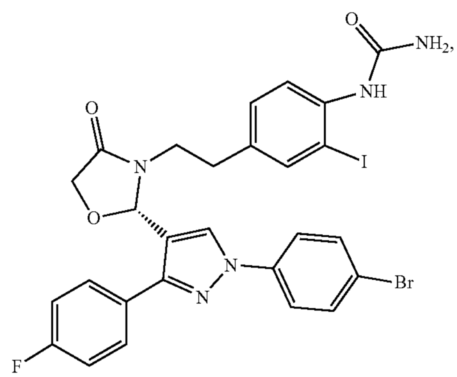
15
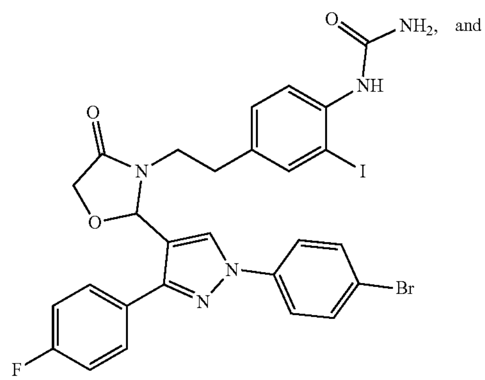
and
16
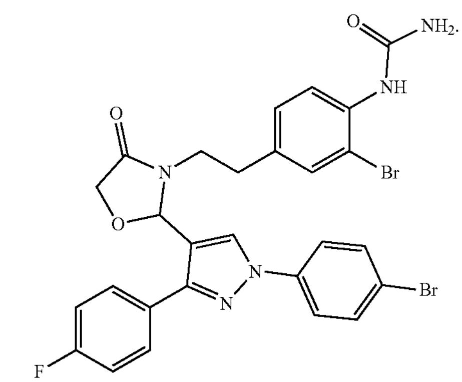
In a third aspect of the present invention, provided is an intermediate shown in formula III,
III
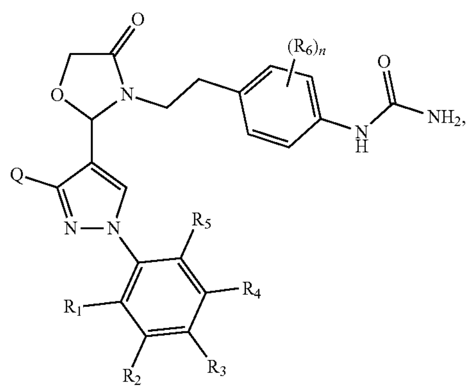
$R_1$, $R_2$, $R_3$, $R_4$, $R_5$, $R_6$, n and Q are as defined in the first aspect of the present invention.
In another preferred embodiment, the intermediate shown in formula III is selected from the group consisting of:
17
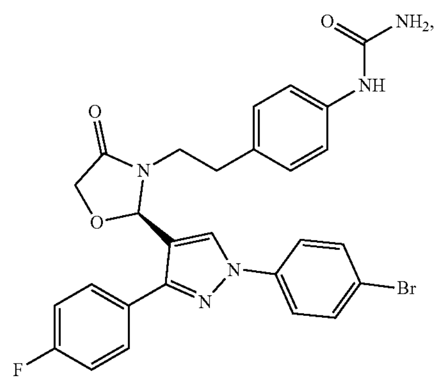
18
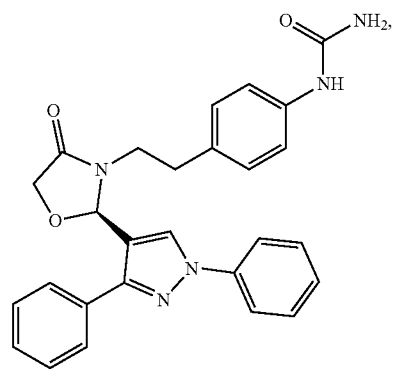
19
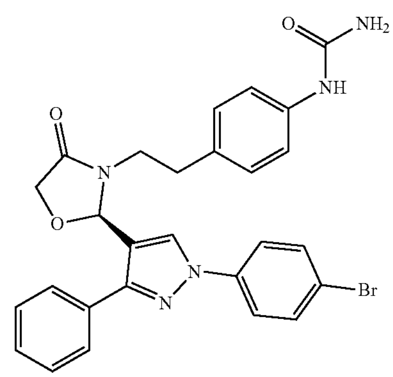
20
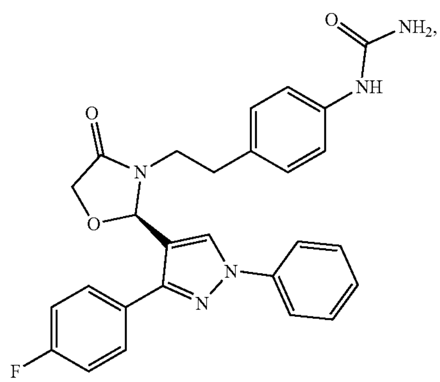

-continued

21

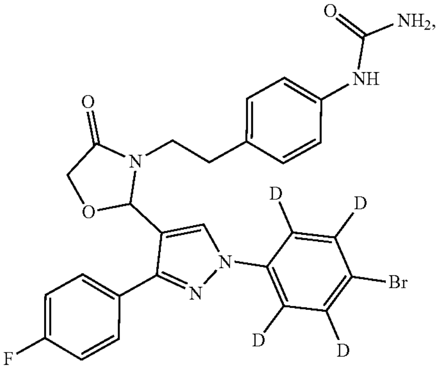

22

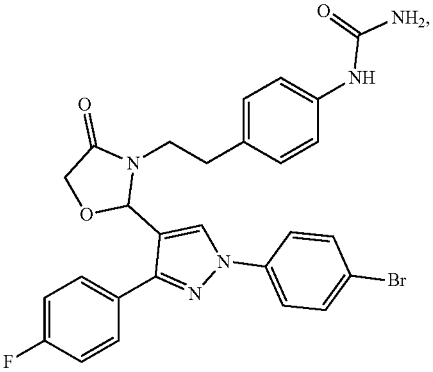

and

35

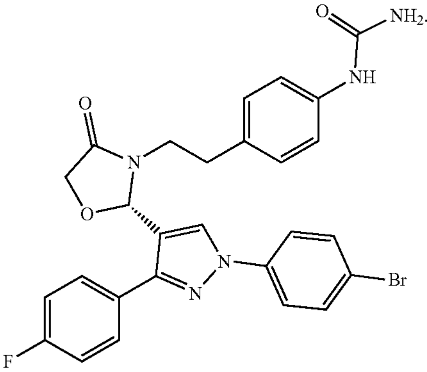

In a fourth aspect of the present invention, provided is a use of an intermediate shown in Formula II as described in the second aspect of the present invention or an intermediate shown in Formula III as described in the third aspect of the present invention for the preparation of a compound of Formula I as described in the first aspect of the present invention, or a pharmaceutically acceptable salt thereof, or a tautomer thereof, or a stereoisomer thereof, or a racemate thereof.

It should be understood that within the scope of the present invention, the above-mentioned technical features of the present invention and the technical features specifically described in the following (such as embodiments) can be combined with each other to form a new or preferred technical solution. Limited by space, it will not be repeated here.

DETAILED DESCRIPTION OF THE INVENTION

After long-term and in-depth research, the present inventors have obtained a new method for the preparation of compounds of formula I and new intermediates for the preparation of compounds of formula I by optimising the process. The method has high yield, high product purity, mild conditions, safe and convenient operation and can avoid the production of intermediates with genotoxicity in the last three steps. Specifically, the method of the present invention starts from the key intermediate of aniline, and after the formation of urea, the inventive hepatitis B virus nucleocapsid inhibitor is synthesised by ring-closure via Ullmann reaction. On this basis, the present invention is completed.

Terms

As used herein, unless otherwise specified, the terms used herein have the ordinary meaning known to those skilled in the art.

As used herein, the term "halogen" refers to F, Cl, Br or I, preferably Cl, Br or I.

As used herein, the term "C1-C6 alkyl" refers to straight or branched alkyl groups comprising 1-6 carbon atoms, such as methyl, ethyl, propyl, isopropyl, butyl, isobutyl, tert-butyl, neopentyl, tert-pentyl, and the like.

As used herein, the term "C6-C10 aryl" refers to an aromatic ring group with 6-10 carbon atoms and without heteroatoms on the ring, such as phenyl, naphthyl, and the like.

The term "more" means 2, 3 or 4.

The term "6-10 heteroaryl" refers to an aromatic heterocyclic ring containing 1-3 heteroatoms selected from N, O and S and 3-9 carbon atoms. Non-limiting examples include: furanyl, thienyl, pyridinyl, pyrazolyl, pyrrolyl, N-alkylpyrrolyl, pyrimidinyl, pyrazinyl, imidazolyl, tetrazolyl and the like. Said heteroaryl ring may be fused with an aryl, heterocyclyl or cycloalkyl ring, wherein the ring attached to the parent structure is the heteroaryl ring. The heteroaryl group may be optionally substituted or unsubstituted.

The term "room temperature" means 10-40° C., preferably 15-30° C., more preferably 20-30° C.

Compound of Formula I

I

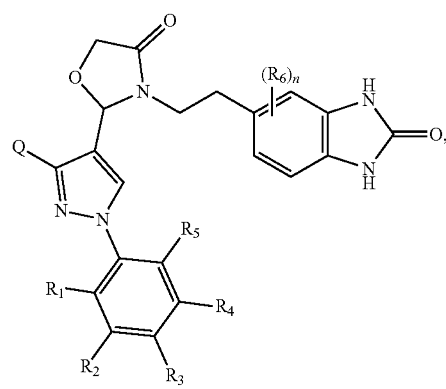

$R_1$, $R_2$, $R_3$, $R_4$, $R_5$, $R_6$, n and Q are as defined above.

The compound of formula I produced by the synthetic method of the present invention has significantly higher yield and higher purity, and the synthesis process is simple and does not involve operations with a high risk factor such as nitration, and avoids the use of process operations such as column chromatography, which are unsuitable for large scale production. The intermediates of the last three steps for the synthesis of the compound are all negative by AMES, and none of them contained genotoxicity. The risk of excess genotoxic impurities in the compound was reduced.

As used herein, the term "pharmaceutically acceptable salt" refers to a salt of a compound of the invention formed with an acid or base suitable for use as a drug. Pharmaceutically acceptable salts include inorganic and organic salts. Preferred class of salts are those formed by the compounds of the present invention with acids. Acids suitable for the formation of salts include, but are not limited to: inorganic acids such as hydrochloric acid, hydrobromic acid, hydrofluoric acid, sulphuric acid, nitric acid, and phosphoric acid, etc.; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulphonic acid, ethanesulfonic acid, p-toluenesulphonic acid, benzenesulphonic acid, naphthalenesulphonic acid, etc.; and amino acids such as proline, phenylalanine, aspartic acid, glutamic acid, etc.

Another preferred class of salts are salts formed by the compounds of the present invention with a base, such as alkali metal salts (e.g., sodium or potassium salts), alkaline earth metal salts (e.g., magnesium or calcium salts), ammonium salts (e.g., lower alkanolammonium salts, and other pharmaceutically acceptable amine salts), such as methylamine salts, ethylamine salts, propylamine salts, dimethylamine salts, trimethylamine salts, diethylamine salts, triethylamine salts, tert-butylamine salts, ethylenediamine salts, hydroxyethylamine salts, dihydroxyethylamine salts, trihydroxyethylamine salts, and amine salts formed by morpholine, piperazine, and lysine, respectively.

General Synthesis Methods:

Take compound

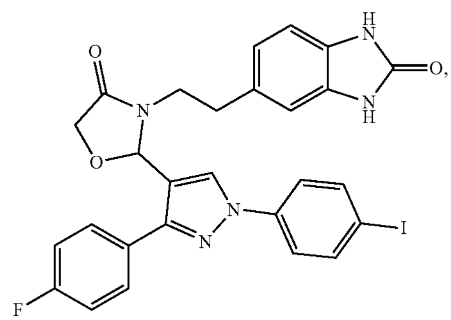

8 as an example, please see the disclosure of Example 6 of WO2017173999 A1, wherein the compound is prepared as follows:

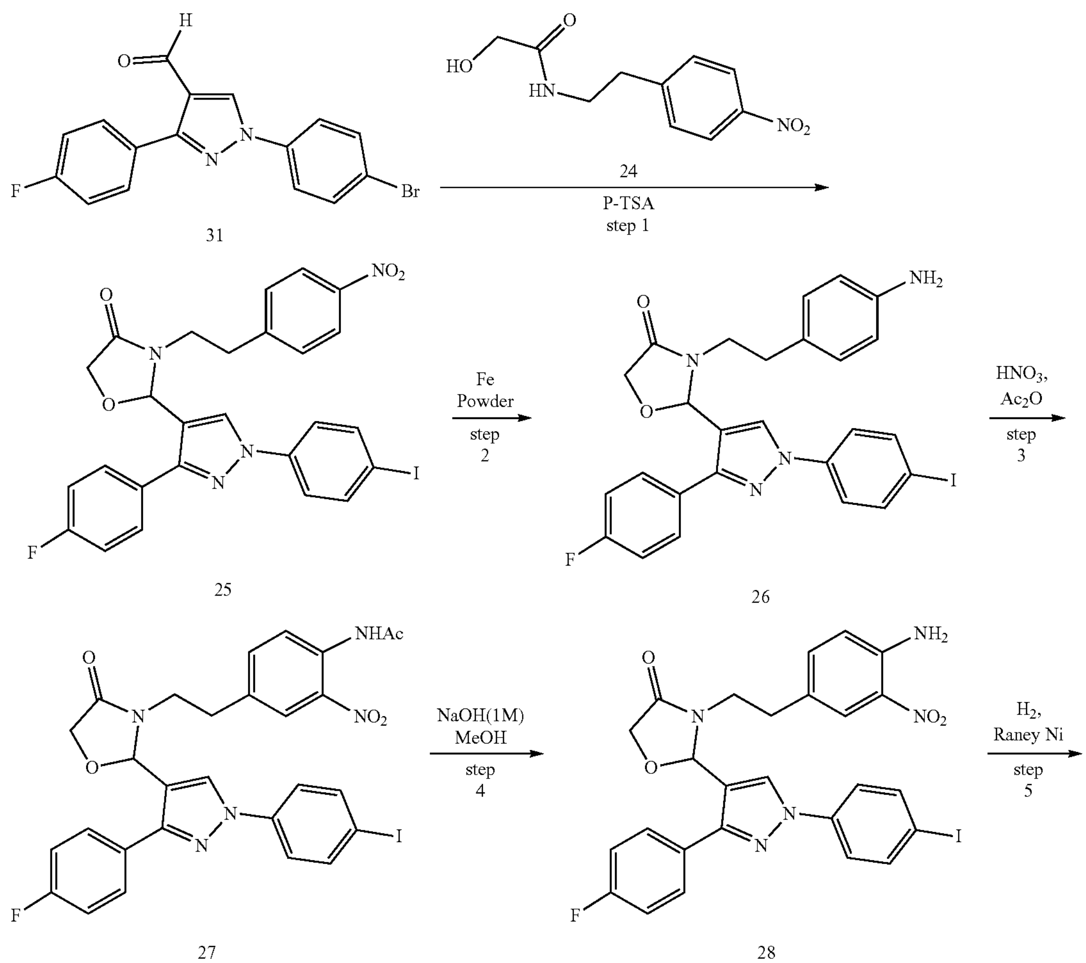

31
24
25
26
27
28

-continued

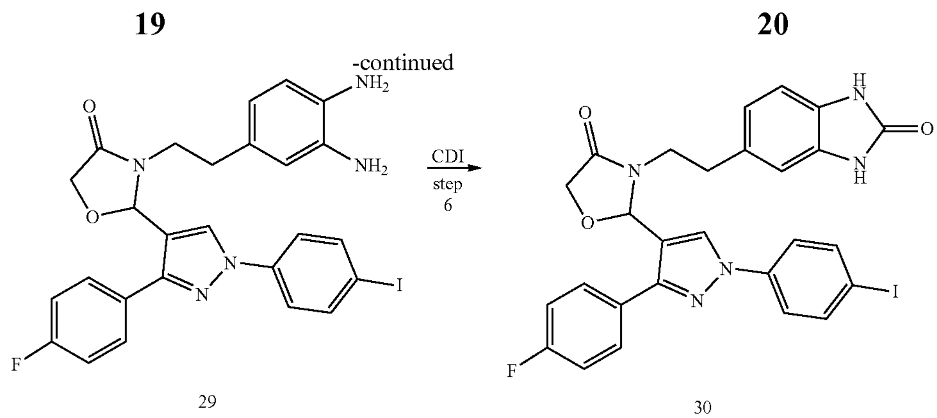

29

30

As shown in Example 6 of WO2017173999 A1, Step 3 requires acetic anhydride as a solvent and concentrated nitric acid for the nitration reaction, which is carried out under relatively vigorous reaction conditions. The nitration reaction generates a large amount of heat and stands a potential risk of multiple nitrations, which is not conducive to scaling up production, and there is a high safety risk in the later production.

As shown in Example 6 of WO2017173999 A1, starting from intermediate 26, four steps are required to generate the final ring-closure reaction, and the yields of the four steps are 65.3%, 32.6%, 69.3%, and 24.9%, respectively, which are low. And the last reaction step requires column chromatography purification to obtain the product, which is not suitable for the demand of large-scale production.

As shown in Example 6 of WO2017173999 A1, in the above preparation route, the intermediates 27, 28, 29 generated in Steps 3-5 all contain nitrobenzene or o-phenylenediamine structures, which are potentially risky. Any kind of intermediates in APIs requires the development of ppm level analysis methods and strict control, and the residues of the above intermediates will affect the quality control of APIs, and if not completely removed, they cannot meet the strict clinical requirements and are not conducive to the large-scale preparation of safe and compliant clinical samples.

Synthesis Method of the Present Invention

Unlike the existing synthetic methods described above, the present invention employs the synthetic route shown below, taking compound 4

4

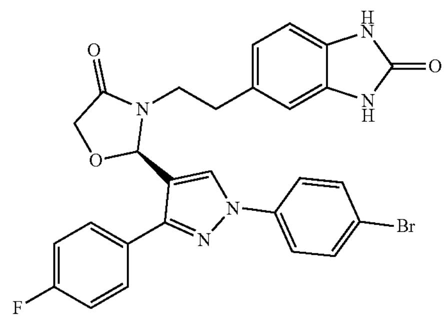

as an example:

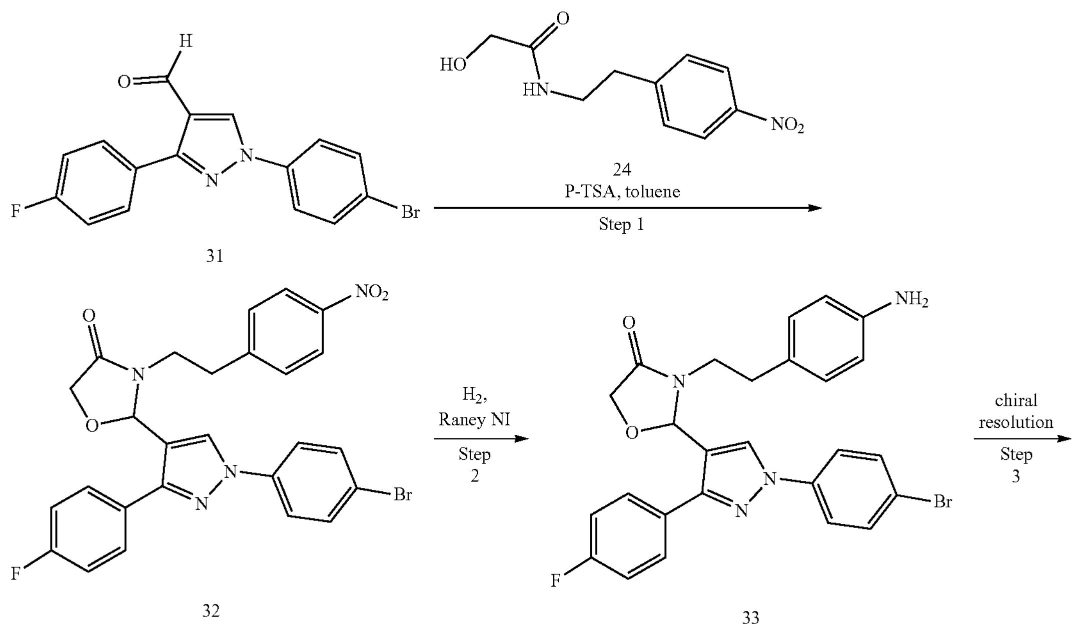

31

32

33

-continued

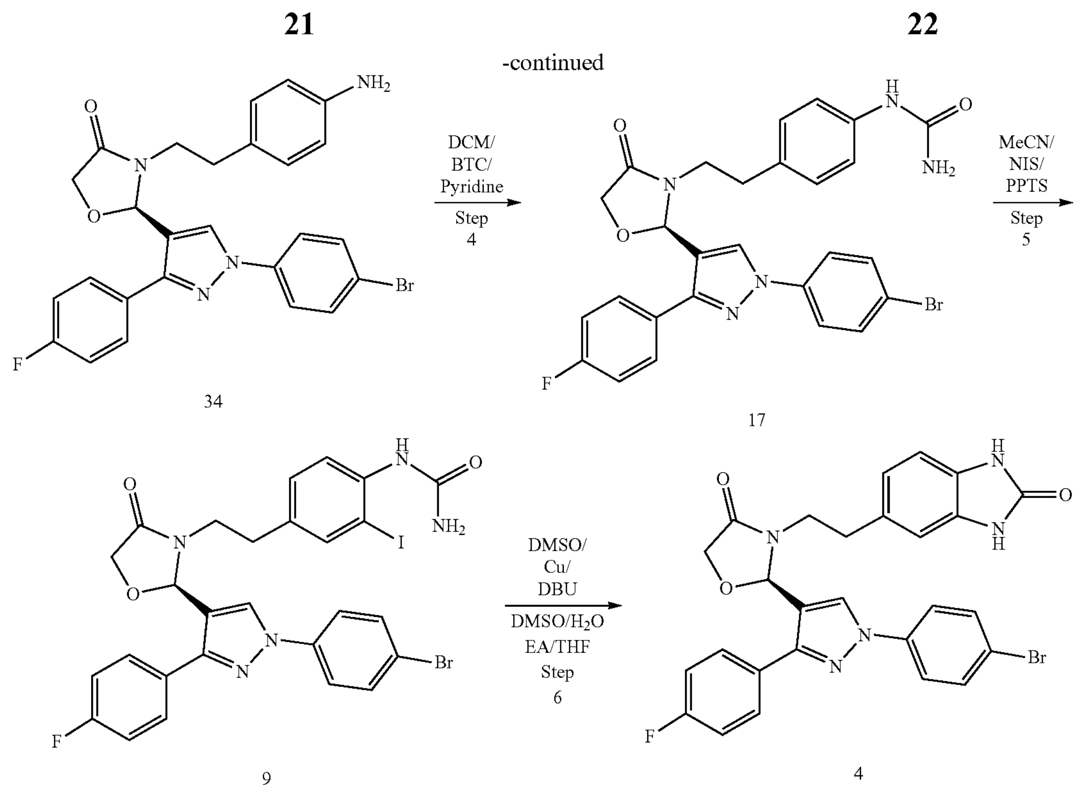

34

17

9

4

It comprises the following steps:

1) Compound 24 and compound 31 are catalysed by p-toluenesulfonic acid to form compound 32;
2) Compound 32 is reduced by hydrogen to afford compound 33 under the catalysis of Raney nickel;
3) The racemic compound 33 is separated using chiral chromatography or supercritical fluid chromatography (SFC) or other separation means to obtain chirally pure compound 34;
4) Compound 34 together with triphosgene and ammonia in the presence of pyridine react to produce compound 17;
5) Compound 17 is catalysed by pyridine p-toluenesulfonate to form compound 9;
6) Compound 9 is reacted under the catalysis of copper powder and DBU to form compound 4;

wherein, step 1) is carried out in a single solvent or a combination of solvents, including but not limited to toluene, xylene, methanol, ethanol, and combinations thereof. Preferably, toluene.

The acid in step 1) includes, but is not limited to, p-toluenesulfonic acid, methanesulfonic acid, trifluoromethanesulfonic acid, camphorsulfonic acid, preferably p-toluenesulfonic acid.

The mass ratio of the amount of the acid in step 1) to compound 31 is 0.1-1, preferably 0.25.

The molar ratio of the amount of compound 24 in step 1) to compound 31 is 0.90 eq. −1.5 eq., preferably 1.2eq.

The temperature in step 1) is 60-120° C., preferably 110-120° C.

The reduction of nitro in step 2) can be carried out with reducing agents such as iron powder, zinc powder, sodium hydrosulfite, tin dichloride, etc., or by catalytic hydrogenation.

The catalyst used in the catalytic hydrogenation reaction of nitro in step 2 includes but is not limited to palladium carbon, platinum carbon, Raney nickel, palladium carbon hydroxide, preferably Raney nickel.

The catalytic hydrogenation reaction of the nitro group in step 2), if Raney nickel is used, has a mass ratio relative to compound 32 of 0.1-0.5, preferably 0.3.

Step 2) is carried out in a single solvent or a combination of solvents including, but not limited to, ethanol, methanol, ethyl acetate, toluene, xylene, methyltetrahydrofuran, tetrahydrofuran and water, preferably ethyl acetate.

It should be understood that the compounds of formula IV of the present invention (e.g., compound 33) may be produced by the preparation methods described above, or by methods known in the prior art, or may also be commercially available.

In contrast to the existing synthetic methods described above, the synthetic method of the present invention produced the compound of formula I represented by compound 4 by optimising the original step 3) and the subsequent processes. The yields of the three steps of the reaction were 90.86%, 86.9% and 83.5%, respectively, with an overall yield of 65.9%. The total yield was significantly higher than the total yield of 44.6% for the four-step reaction (yields of 70%, 93.8%, 90%, 75.4%, respectively) of the synthesis of racemates in the prior art. In the synthetic method of the present invention, intermediate 17 and intermediate 9 were tested to be free of warning structures, effectively avoiding the effect of relevant impurity residues on the compound of formula I represented by compound 4. The last three steps of the present method avoided the use of column chromatography purification, which effectively improved the purification efficiency. The method also avoids the operation with high safety risk such as nitration in the original synthesis process, which is more conducive to scale-up production. The method has the advantages of high yield, controllable impurities, convenient operation and suitable for kilogram-scale preparation.

Compound of Formula II and Compound of Formula III

II

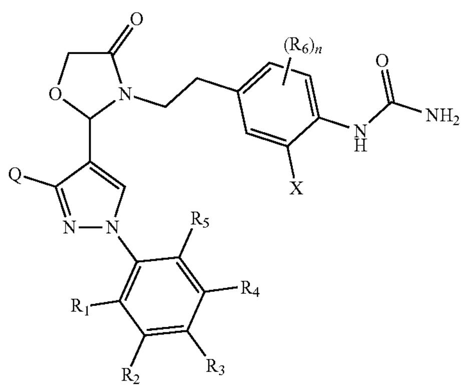

$R_1$, $R_2$, $R_3$, $R_4$, $R_5$, $R_6$, n, X and Q are as defined above.

III

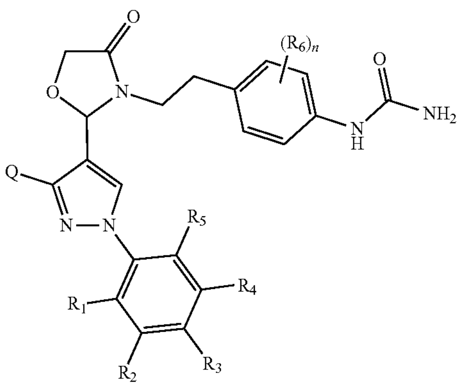

$R_1$, $R_2$, $R_3$, $R_4$, $R_5$, $R_6$, n and Q are as defined above.

It has been identified that most of the compounds of formula II and compounds of formula III of the present invention do not contain warning structures such as primary aniline or nitrobenzene, which is very conducive to the quality control of the target product of compounds of formula I.

Compared to the prior art, the present invention has the following main advantages:

(1) The method has the advantages of high yield, safe process operation, easy industrialization, mild conditions, and the chemical synthesis step does not require column chromatography separation; and the method also has the advantage of low cost;

(2) The method avoids the use of intermediates with warning structures, which effectively reduces the difficulty in controlling impurities in the preparation process and the final product.

The present invention is further described below in conjunction with specific embodiments. It is to be understood that these examples are intended to illustrate the invention only and not to limit the scope of the invention. The experimental methods in the following examples that do not specify specific conditions are usually based on conventional conditions or conditions recommended by the manufacturer. Unless otherwise specified, percentages and parts are calculated by weight.

Unless otherwise defined, all professional and scientific terms used herein have the same meanings as commonly understood by those skilled in the art. In addition, any methods and materials similar or equivalent to those described can be applied to the method of the present invention. The preferred implementation methods and materials described herein are for demonstration purposes only.

Example 1 Synthesis of Compound 32

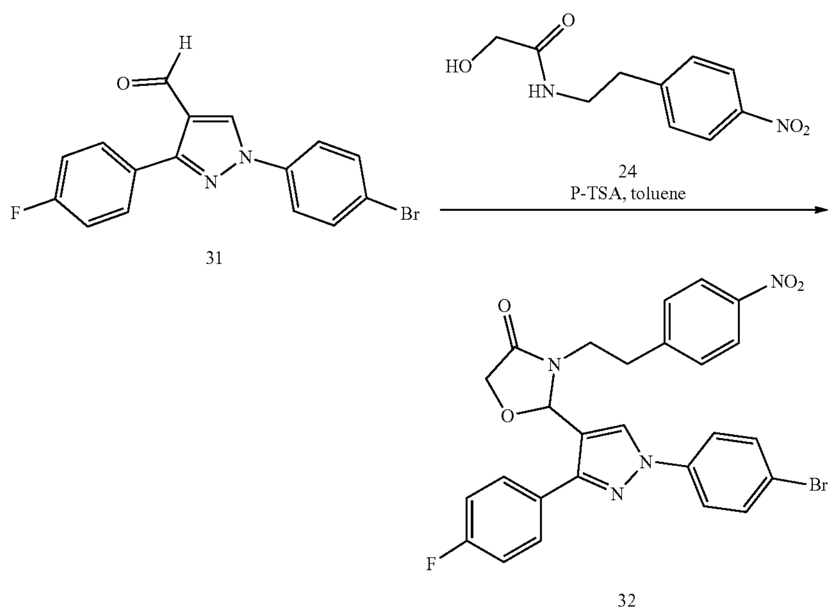

31

32

To a reactor was added toluene (303 kg), Compound 31 (35 kg) and p-toluenesulfonic acid (7 kg) sequentially at room temperature, raised the temperature to 105~115° C., and stirred with water separation for 1 h. The temperature was lowered to 60~80° C. before compound 24 (28.33 kg) was added to the reactor, then raised to 110~120° C., and the reaction was carried out with reflux and water separation for 12 hours. The temperature was lowered to 78~80° C. before additional p-toluenesulfonic acid (180 g) and compound 24 (505 g) were added. The reaction continued to be heated and refluxed with water separation for 7-8 h. HPLC control showed that most of compound 31 was converted completely; then the reaction system was cooled down to 50-55° C. followed by the addition of methanol (35.4 kg) and stirred for 2 h. The reaction system was then cooled down, filtered, and the filter cake was rinsed with a small amount of toluene/methanol solution. The filter cake was dried to give 40.5 kg of compound 32 with a yield of 72.5% and HPLC purity of 98%. MS: $[M+H]^+$=551.4/553.4

Example 2 Synthesis of Compound 33

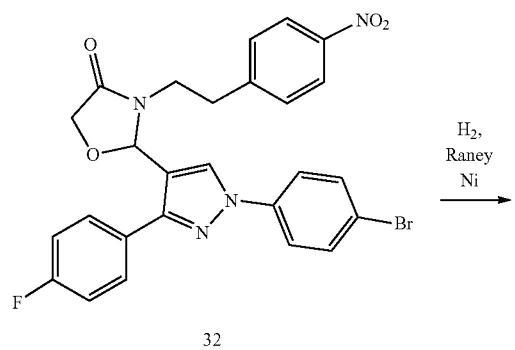

32

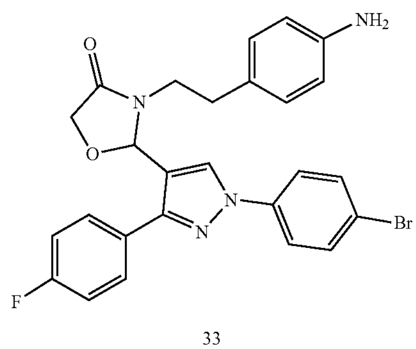

33

To a reactor was added ethyl acetate (8 L), compound 32 (178.3 g, 1.0 eq.), triethylamine (80 mL) and Raney nickel (48 g, 27%) at room temperature. The reaction system was replaced with hydrogen gas three times and the reaction was carried out at room temperature for 8 h. HPLC control showed complete conversion of compound 32. After filteration, the filtrate was concentrated to give 160.4 g of compound 33. The yield was 95. 1% and HPLC purity was 98. 2%. MS: $[M+H]^+$=521.5/523.5

Example 3 Separation of Compound 33

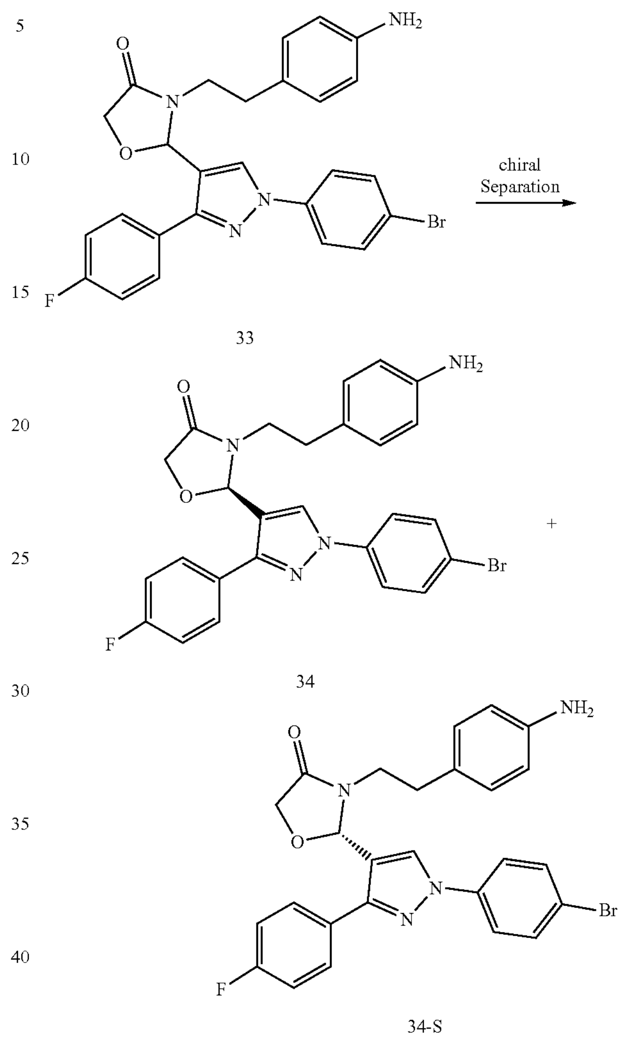

33

34

34-S 5 g of racemic compound 33 was taken and separated using chiral chromatography with methanol as the main mobile phase. After chiral separation, 1.3 g of compound 34 (ee>99%) and 1.78 g of compound 34-S were obtained.

Example 4. Synthesis of Compound 17

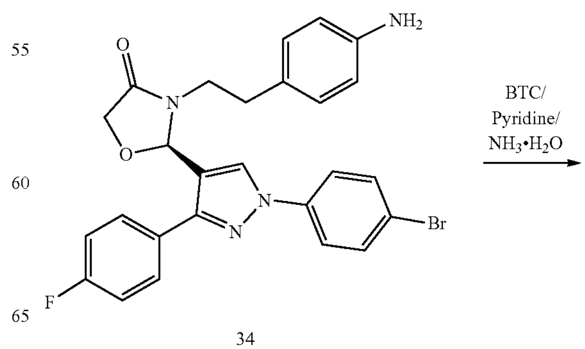

34

-continued

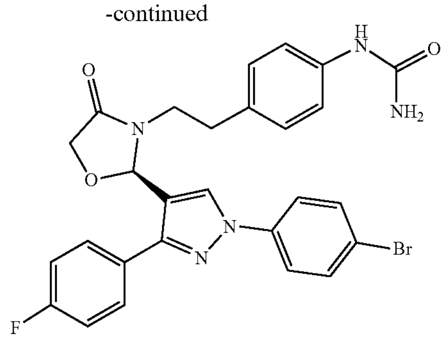

17

A solution of triphosgene (BTC) (170.75 g, 0.58 mol) in dichloromethane (6 L) was configured at −10° C. To the above solution of triphosgene in dichloromethane was slowly added dropwise a solution of compound 34 (600 g, 1.15 mol) in dichloromethane (4.8 L). The reaction was stirred for 30 min. Below −5° C., a solution of pyridine (273.07 g, 3.45 mol) in dichloromethane (1.2 L) was added dropwise, and the reaction solution continued stirring for 20 min after addition. Below −5° C., ammonia (0.9 L) was added dropwise and the reaction continued stirring for at least 30 minutes.

HPLC showed that the reaction was complete, and the reaction was washed twice with water and then concentrated. The resulting product was dissolved in ethyl acetate and pulped with n-heptane. The filter cake was collected and dried to give 590 g of compound 17, with a yield of 90.86% and purity of 98.45%. MS: $[M+H]^+$=563.01/565.02

Example 5. Synthesis of Compound 9

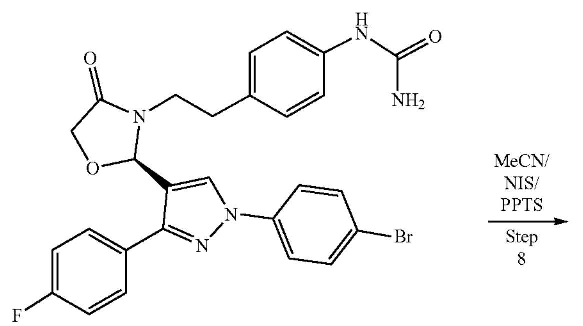

17

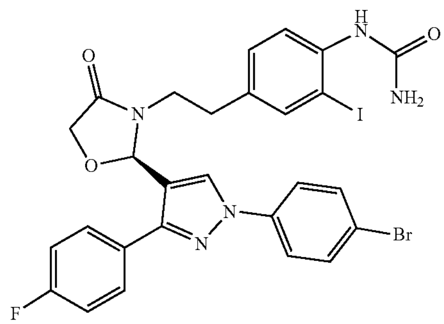

9

Compound 17 (190 g, 0.337 mol) was dissolved in acetonitrile (1.3 L), and PPTS 25 (i.e., pyridine p-toluenesulfonate) (42.3 g, 0.168 mol), and NIS (i.e., N-iodosuccinimide) (90.88 g, 0.4 mol) were added. After reacting at 56° C. overnight, a large amount of solid precipitated. After passing HPLC test, the reaction was cooled down to 20-30° C. and washed by adding 5% sodium sulfite solution. The solid was collected by filtration and the resulting solid was washed with MTBE (methyl tert-butyl ether), then dried to give 202 g of compound 9 with a yield of 86.9% and purity of 98.75%. MS: $[M+H]^+$=689.84/691.84

Example 6. Synthesis of Compound 4

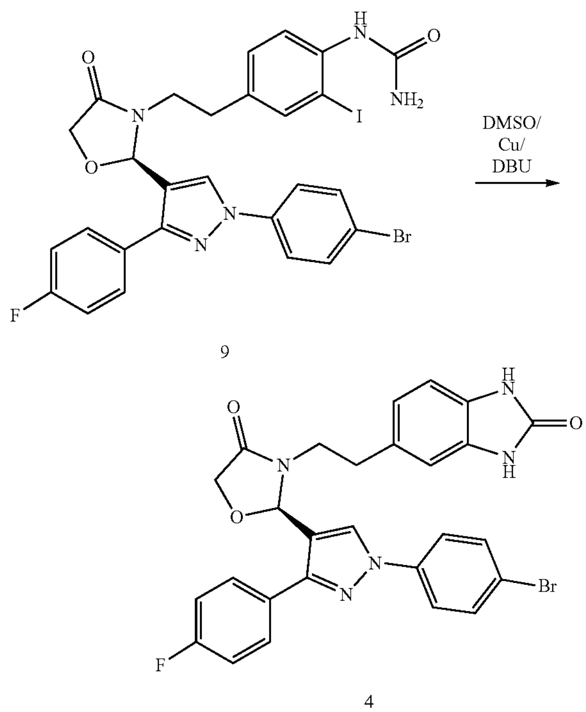

9

4

To a solution of Compound 9 (200 g, 0.29 mol) in DMSO (1.6 L) was added copper powder (18.5 g, 0.29 mol) and 1,5-diazabicyclo[5.4.0]undec-5-ene (48.5 g, 0.319 mol), and reacted at 106° C. for 2 h. After passing the HPLC monitoring, activated carbon was added. After filtration, the filtrate was collected. The filtrate was added to 7% aqueous acetic acid solution and stirred for 20 minutes. After filtration, the filter cake was collected. The resulting filter cake was dissolved with ethyl acetate and THF. The organic phase was washed with 7% diluent acetic acid and 7% sodium bicarbonate (2.0 L), respectively. The resulting organic phase was dried with anhydrous sodium sulfate. The organic solvent was removed by concentration. After pulping in acetone and filtration, the filter cake was collected and dried to give 136 g of compound 4, yield: 83.5%, purity: 99.33%.

MS: $[M+H]^+$=562.5/563.4; $^1$H NMR (600 MHZ, DMSO-$d_6$) δ 10.48-10.43 (m, 2H), 8.73 (s, 1H), 7.93-7.87 (m, 2H), 7.75-7.69 (m, 2H), 7.67-7.60 (m, 2H), 7.33-7.26 (m, 2H), 6.73 (d, J=7.8 Hz, 1H), 6.64 (s, 1H), 6.61 (dd, J=8.0, 1.6 Hz, 1H), 6.03 (d, J=1.8 Hz, 1H), 4.30-4.21 (m, 2H), 3.70 (dt, J=14.3, 7.3 Hz, 1H), 2.92 (dt, J=14.3, 7.3 Hz, 1H), 2.69 (dt, J=14.5, 7.4 Hz, 1H), 2.62 (dt, J=14.1, 70 Hz, 1H).

Example 7. Synthesis of Compound 4

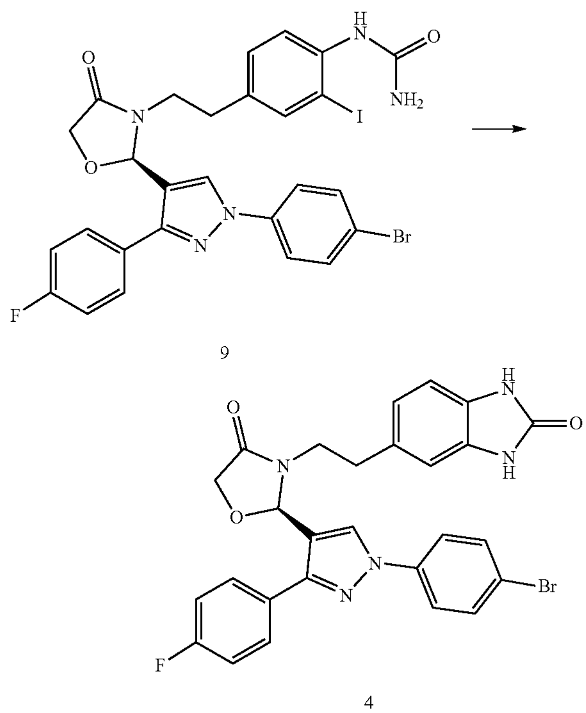

9

4

Compound 9 (1 g, 1.45 mmol), cuprous oxide (10 mg, 0.07 mmol.), ligand L19 (20 mg, 0.07 mmol), and cesium carbonate (1.89 g, 5.79 mmol) were dissolved in dimethylsulfoxide and the reaction was carried out at 75° C. for 24 hours. After HPLC monitoring showed the completion of the reaction, the reaction was cooled down to room temperature; 50 mL of water and 50 mL of ethyl acetate were added and partitioned. After the aqueous phase was extracted three times with ethyl acetate, the combined organic phases were dried and concentrated to obtain the crude product. The crude product was pulped in a mixture of ethyl acetate and petroleum ether to give the end product of compound 4 (520 mg, purity of 95. 15%, a yield of 65%) MS: $[M+H]^+$=562.1/564.1

In the present invention, ligand L19 is $N^1$,$N^2$-bis(thiophen-2-ylmethyl)oxalamide.

Compared with Example 3 of WO2017173999 A1, it needs to go through 4 steps of nitration, hydrolysis, reduction and CDI ring-closure to generate the final ring closure reaction starting from the common intermediate (Compound 34 in the present invention), and the yields of the 4 steps of the reaction are 70%, 94%, 90%, and 75%, with a total yield of 44%, which has a longer synthesis step and a lower yield. In addition, the last step of the reaction requires column chromatography purification to obtain the product, which is not very suitable for the needs of large-scale production. The synthetic route described in the present invention requires only three steps, and the total synthetic yield can reach up to 66%. Both the production efficiency and the total yield are significantly improved.

Compared with Example 3 of WO2017173999 A1, the intermediates used in the last three steps are similar to Example 6 of the patent, and both contain the warning structures of nitrobenzene or o-phenylenediamine, which is potentially risky. All relevant intermediates in APIs require the development of ppm level analysis methods and strict control. Such routes are not conducive to the large scale preparation of safety and compliant clinical samples. The synthetic route of the present invention avoids the use of compounds with similar structures, and Compound 17 and Compound 9 are negative in Ames assays, providing a better safety. Accordingly the control in production becomes easier.

Example 8. Synthesis of Compound 4

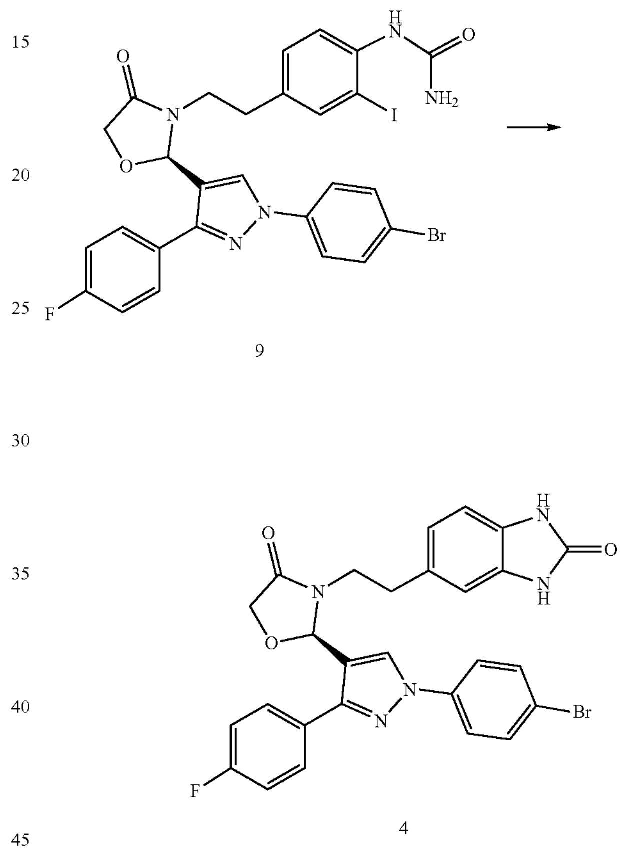

9

4

Compound 9 (1.0 g, 1.45 mmol), cuprous chloride (7.17 mg, 0.072 mmol), ligand L21 (18 mg, 4.35 mmol) and cesium carbonate (1.416 g, 4.35 mmol) were dissolved in dimethylsulfoxide (10 mL) and the reaction was carried out at 70° C. for 16 hours. After HPLC monitoring showed the completion of the reaction, the reaction was cooled down to room temperature before 50 mL of water and 50 mL of ethyl acetate were added, and then partitioned. After the aqueous phase was extracted three times with ethyl acetate, the combined organic phases were dried and concentrated to obtain the crude product. The crude product was pulped in a mixture of ethyl acetate and petroleum ether to give the end product of compound 4 (650 mg, purity 99.76%, yield 80%) MS: [M+H]+=562.0/564.1

In the present invention, ligand L21 is $N^1$,$N^2$-bis(furan-2-ylmethyl)oxalamide.

A summary of the comparison of Examples 6-8 of the present invention with Example 3 of WO2017173999 A1 (Comparative Example 1) and Example 6 (Comparative Example 2) is shown in the table below.

| | Example 6 | Example 7 | Example 8 | Comparative Example 1 | Comparative Example 2 |
|---|---|---|---|---|---|
| Synthesis steps from compound 34 to product | 3 | 3 | 3 | 4 | 4 |
| Total synthetic yield from compound 34 to product | 65.9% | 51.3% | 63.2% | 44.6% | 3.7% |

Example 9. Synthesis of Compound 35

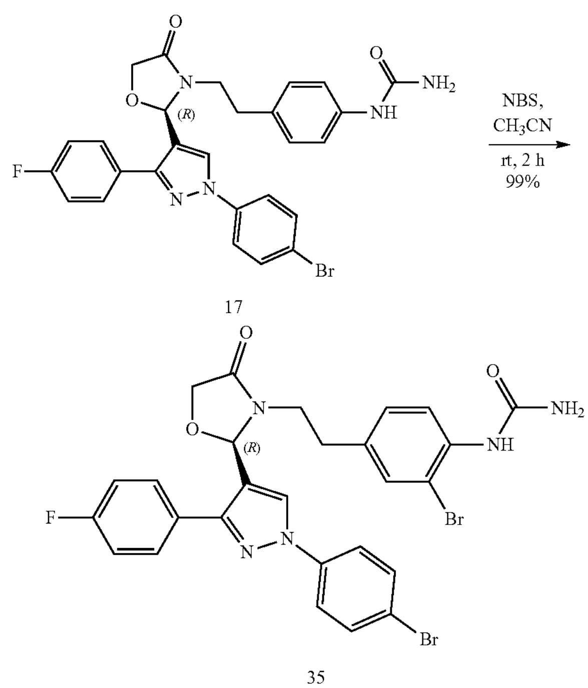

17

35

Compound 17 (15 g, 2.66 mmol, 1.0 eq) was dissolved in acetonitrile (20 mL), then NBS (570 mg, 3.19 mmol, 1.2 eq) was added and the reaction solution was stirred at room temperature for 2 hours. The reaction solution was diluted with ethyl acetate (40 mL) and then washed with saturated aqueous sodium sulfite solution (20 mL×2) and saturated aqueous sodium bicarbonate solution (20 mL×2), respectively. The separated organic phase was washed with saturated saline, dried with anhydrous sodium sulfate and concentrated to give compound 35 (1.7 g, 99%) as a yellow solid.

LCMS: [M+H]+=644.1

Example 10. Synthesis of Compound 4

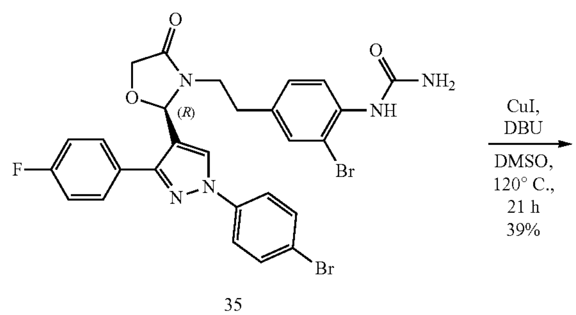

35

-continued

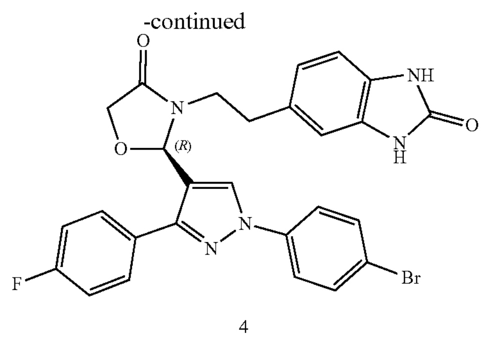

4

To a solution of Compound 35 (100 mg, 0.155 mmol, 1.0 eq) in DMSO (2 mL) was added cuprous iodide (29.6 mg, 0.155 mmol, 1.0 eq) and DBU (47.6 mg, 0.310 mmol, 2.0 eq) sequentially. After three times of nitrogen displacement, the reaction solution was stirred under nitrogen protection at 120° C. for 21 h. After cooling to room temperature, the reaction solution was diluted with ethyl acetate (40 mL), then washed with aqueous citric acid (5%, 10 mL×2) and saturated salt water, respectively, dried with anhydrous sodium sulfate, and concentrated. The residue obtained was purified by silica gel column chromatography (petroleum ether/ethyl acetate=1/20) to give Compound 4 (34 mg, 99% purity) as a white solid. LCMS: $[M+H]^+$=562.1

$^1H$ NMR (400 MHz, $CDCl_3$) δ 9.88-9.48 (m, 2H), 7.85 (s, 1H), 7.62-7.52 (m, 6H), 7.14-7.10 (m, 2H), 6.79-6.63 (m, 3H), 5.90 (s, 1H), 4.43-4.26 (m, 2H), 3.96-3.80 (m, 1H), 3.08-2.96 (m, 1H), 2.78-2.68 (m, 2H)

Example 11. Synthesis of Compound 37

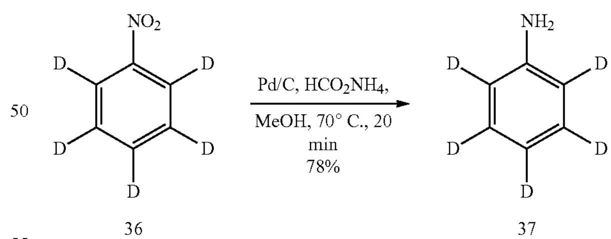

36 37

To a solution of compound 36 (2.5 g, 19.51 mmol, 1.0 eq) in methanol (30 mL) was added ammonium formate (6.2 g, 97.55 mmol, 5.0 eq), and the reaction solution was stirred at room temperature for 10 minutes. The reaction solition was added withpalladium carbon (10%, 300 mg), heated to 70° C. and stirred for 20 minutes. After cooling to room temperature, the reaction solution was filtered and the filtrate was concentrated. The residue obtained was purified by fast silica gel column chromatography (petroleum ether/ethyl acetate=5/1) to give compound 37 (1.5 g, 78%) as a colourless oil. LCMS: $[M+H]^+$=99.2

Example 12. Synthesis of Compound 38

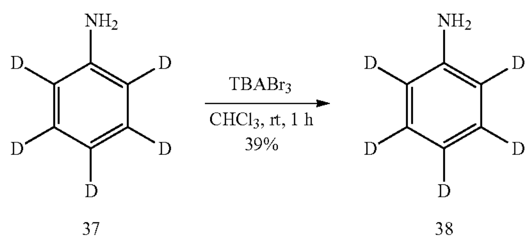 [SMILES: [2H]c1c([2H])c([2H])c(N)c([2H])c1[2H] ; [2H]c1c([2H])c([2H])c(N)c([2H])c1[2H]]

37

38

To a solution of compound 37 (3.7 g, 37.693 mmol, 1.0 eq) in chloroform (75 mL) was added tetrabutylammonium tribromide (19 g, 39.578 mmol, 1.05 eq). The reaction solution was stirred at room temperature for 1 hour. Then the reaction solution was poured into saturated aqueous sodium bicarbonate solution to pH 8. The separated organic phase was washed with saturated salt water, dried with anhydrous sodium sulfate and concentrated, and the resulting residue was purified by silica gel column chromatography (neutral alumina, petroleum ether/ethyl acetate=20/1 to 12/1) to give compound 38 (2.6 g, 39%) as a brown solid. LCMS: $[M+H]^+=176.0$ Example 13. Synthesis of Compound 39

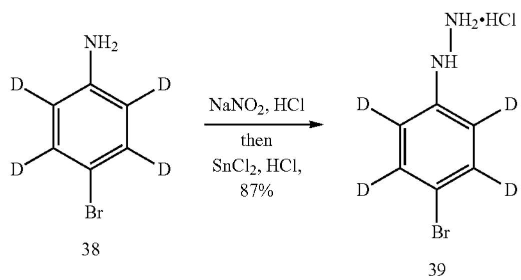

38

39

To a solution of compound 38 (1.5 g, 8.523 mmol, 1.0 eq) in acetic acid (24 mL) was added concentrated hydrochloric acid (48 mL) and then cooled to −5° C. followed by the dropwise addition of a solution of sodium nitrite (0.7 g, 10.227 mol, 1.2 eq) in water (9 mL). The reaction solution was stirred at −5° C. for 0.5 h before a solution of stannous chloride (4.0 g, 21.307 mmol, 2.5 eq) in concentrated hydrochloric acid (9 mL) was added dropwise, and the temperature of the reaction solution was maintained between 0° C. and 5° C. during the dropwise addition. After the addition, the reaction solution was stirred between 0° C. and 5° C. for 40 min. After filtration, the solid was washed with cooled concentrated aqueous hydrochloric acid solution. The solid was collected and lyophilised to give compound 39 (1.74 g, 87%) as a white solid. LCMS: [M+H]+=191.0

Example 14. Synthesis of Compound 40

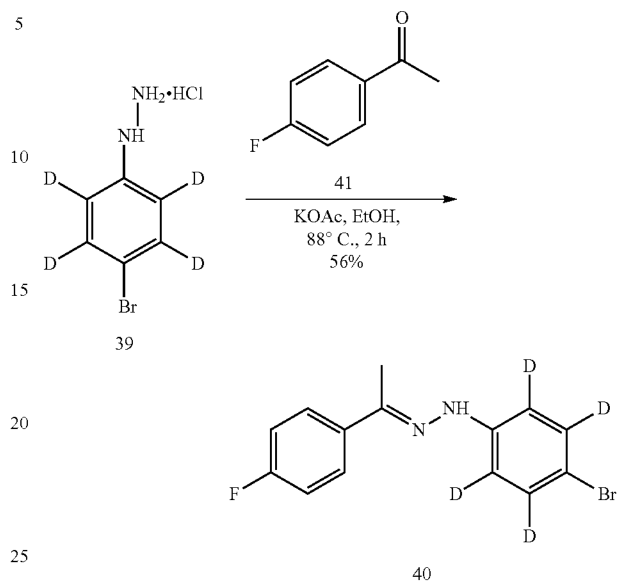

39

40

To a solution of compound 39 (1.74 g, 7.647 mmol, 1.0 eq) in ethanol (8 mL) was added compound 41 (1.05 g, 7.647 mmol, 1.0 eq) and potassium acetate (0.75 g, 7.647 mmol, 1.0 eq) and the reaction solution was stirred for 2 hours at 88° C. After cooling to room temperature, the reaction solution was concentrated; the residue was dissolved with ethyl acetate and then washed with water and saturated salt water, dried with anhydrous sodium sulfate and concentrated; petroleum ether (30 mL) was added to the resulting residue and stirred for half an hour. After filtration, the solid obtained was washed with petroleum ether and dried under vacuum to give compound 40 (1.34 g, 56%) as a brown solid. LCMS: $[M+H]^+=311.1$ Example 15. Synthesis of Compound 42

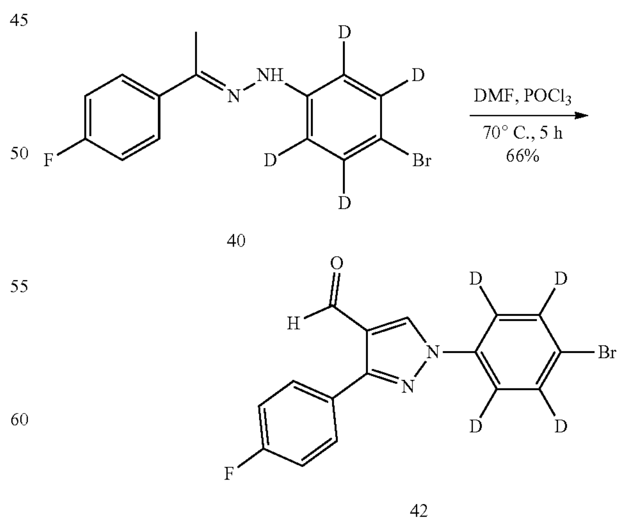

40

42

DMF (692 mg, 9.473 mmol, 2.2 eq) was cooled to 0° C. and then phosphorous trichloride (1.45 g, 9.473 mmol, 2.2 eq) was added dropwise. After addition, the reaction solution was stirred at 0° C. for half an hour and then a solution of compound 40 (1.34 g, 4.306 mmol, 1.0 eq) in DMF (9 mL) was added dropwise to the above reaction solution. After dropwise addition, the reaction was warmed to room temperature and stirred for 40 minutes, then warmed to 70° C. and stirred for 5 hours. After cooling to room temperature, the reaction solution was poured into ice water. After filtration, the solid was collected and the water was removed by azeotropy with toluene, the residue obtained was purified by silica gel column chromatography (petroleum ether/ethyl acetate=5/1 to 2/1) to give compound 42 (1.0 g, 66%) as a white solid. LCMS: [M+H]+=349.0

Example 16. Synthesis of Compound 43

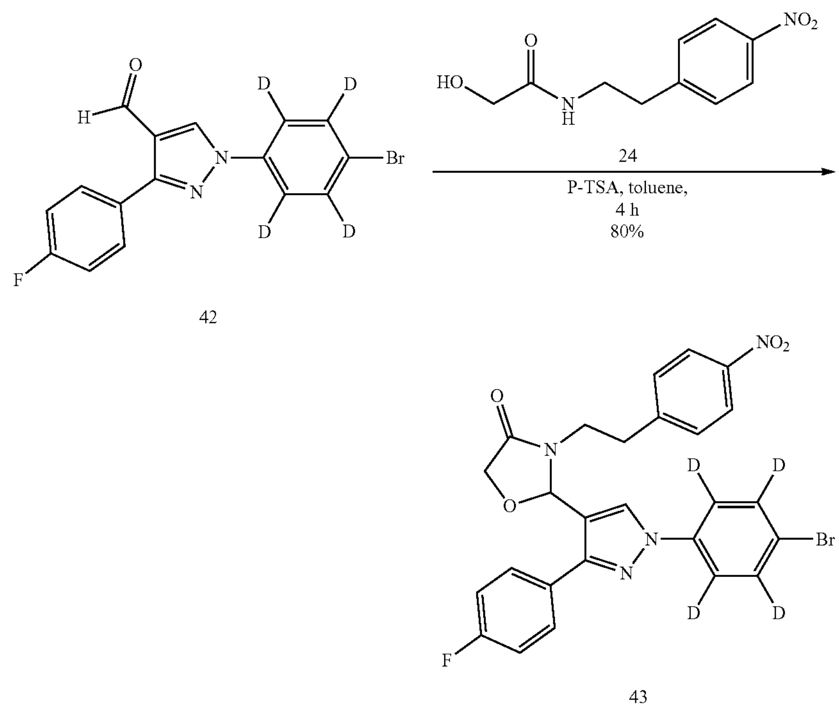

42

43

To a solution of compound 42 (1.0 g, 2.863 mmol, 1.0 eq) in toluene (100 mL) was added compound 24 (0.77 g, 3.436 mmol, 1.2 eq) and p-toluenesulfonic acid monohydrate (0.27 g, 1.432 mmol, 0.5 eq). The reaction solution was stirred at 148° C. for 4 h and then cooled to room temperature, diluted with ethyl acetate (50 mL), washed with saturated salt water, dried with anhydrous sodium sulphate and concentrated; the residue obtained was purified by silica gel column chromatography (petroleum ether/ethyl acetate=1/1) to give compound 43 (1.27 g, 80%) as a white solid. LCMS: [M+H]+=555.0

Example 17. Synthesis of Compound 44

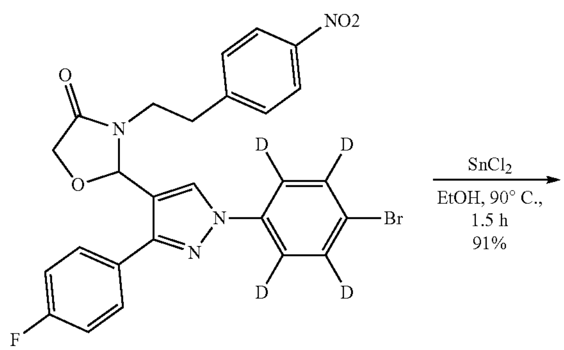

43

-continued

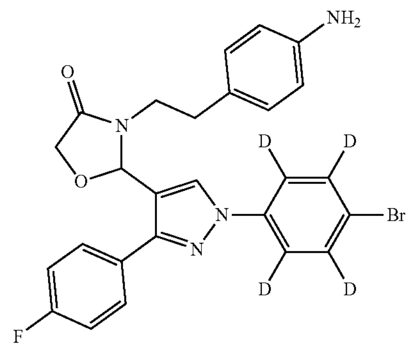

44

To a solution of compound 43 (1.27 g, 2.286 mmol, 1.0 eq) in ethanol (40 mL) was added stannous chloride (10.84 g, 57.166 mmol, 25.0 eq). The reaction solution was stirred at 90° C. for 1.5 h, cooled to room temperature, then adjusted to pH of 9 with aqueous sodium carbonate (2 N) and diluted with ethyl acetate (100 mL). After filtration, the filtrate was washed with water and saturated salt water, dried with anhydrous sodium sulfate and concentrated to give compound 44 (1.1 g, 91%) as a white solid. LCMS: [M+H]+ =525.1

Example 18. Synthesis of Compound 21

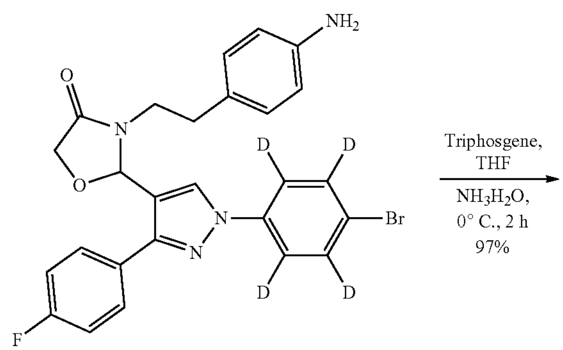

44

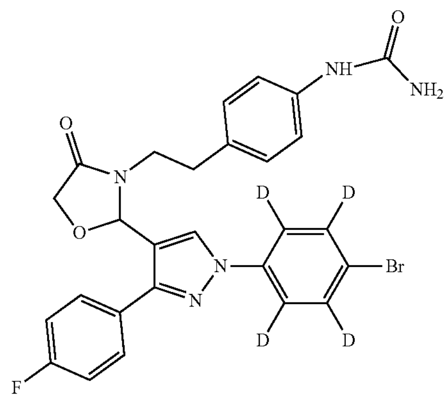

21

Compound 44 (0.9 g, 1.717 mmol, 1.0 eq) was dissolved in tetrahydrofuran (35 mL) and then the reaction was cooled to 0° C. Triphosgene (0.25 g, 0.858 mmol, 0.5 eq) was then added and the reaction was raised to room temperature and stirred for 2 hours at room temperature. The reaction was then cooled to 0° C. and ammonia (2.5 mL) was added. The reaction solution was raised to room temperature and stirred for half an hour and then diluted with ethyl acetate (50 mL), sequentially washed with water and saturated salt water, dried with anhydrous sodium sulfate and concentrated to give compound 21 (0.95 g, 97%) as a white solid. LCMS: $[M+H]^+$=568.1

Example 19. Synthesis of Compound 13

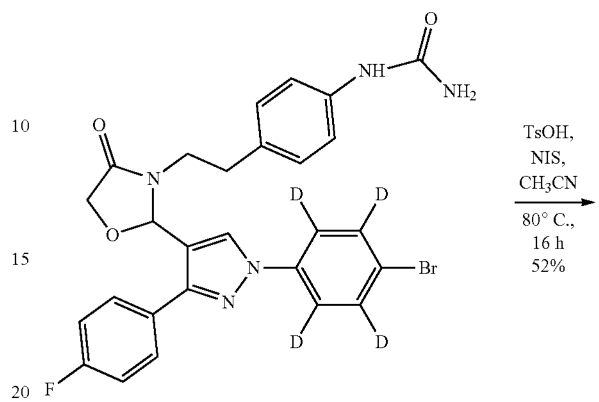

21

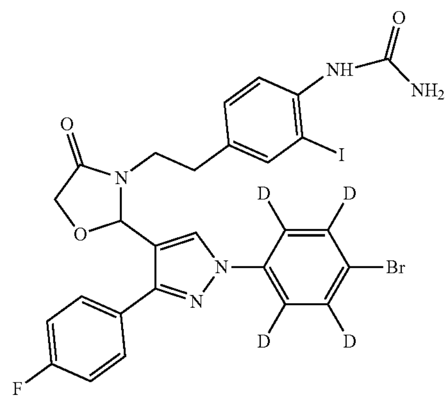

13

To a solution of compound 21 (950 mg, 1.675 mmol, 1.0 eq) in acetonitrile (35 mL) was added p-toluenesulfonic acid monohydrate (64 mg, 0.335 mmol, 0.2 eq) and NIS (565 mg, 2.513 mmol, 1.5 eq), and the reaction solution was stirred for 16 hours at 80° C. After cooling to room temperature, the reaction solution was adjusted to pH 8 with aqueous sodium sulfite solution (0.2 N) and concentrated to remove acetonitrile. The residue was diluted with ethyl acetate (50 mL), washed with saturated salt water, dried with anhydrous sodium sulfate and concentrated, and the resulting residue was purified by silica gel column chromatography (petroleum ether/ethyl acetate=1/1 to 1/5) to give compound 13 (605 mg, 52%) as a brown solid. LCMS: $[M+H]^+$=693.9

Example 20. Synthesis of Compound 5

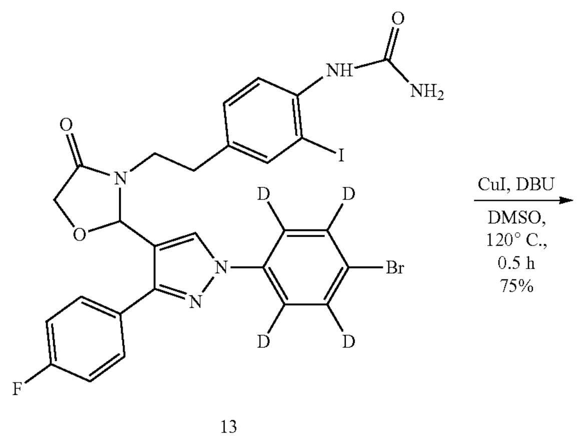

13

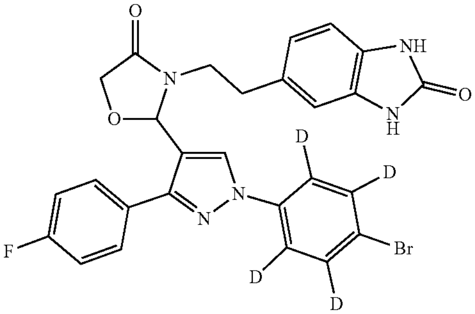

5

To a solution of compound 13 (400 mg, 0.576 mmol, 1.0 eq) in DMSO (30 mL) was added DBU (175 mg, 1.152 mmol, 2.0 eq) and cuprous iodide (109 mg, 0.576 mmol, 1.0 eq) and stirred at 120° C. for 0.5 hours. After cooling to room temperature, the reaction solution was diluted with ethyl acetate (80 mL), washed with water and saturated salt water, dried with anhydrous sodium sulfate and concentrated. The residue obtained was purified by silica gel column chromatography (dichloromethane/methanol=40/1 to 30/1) to give compound 5 (244 mg, purity 99.34%, yield 75%) as a yellow solid. LCMS: $[M+H]^+=566.1$ All documents referred to in the present invention are incorporated by reference herein as if each document is individually incorporated by reference. Further, it should be understood that upon reading the above teaching of the present invention, various amendments or modifications may be made to the present invention by those skilled in the art, and those equivalents also fall within the scope defined by the appended claims of the present invention.

The invention claimed is:

1. A preparation method for a compound of formula I, or a pharmaceutically acceptable salt thereof, or a tautomer thereof, or a stereoisomer thereof, or a racemate thereof, comprising steps of:

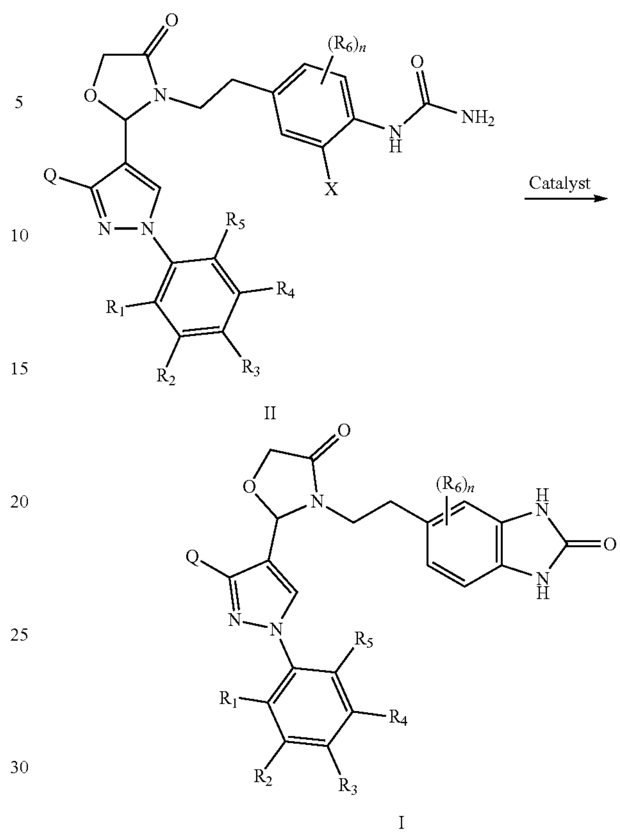

II

I 1) in the presence of a catalyst, subjecting a compound of formula II to cyclization to obtain a compound of formula I;

wherein, $R_1$, $R_2$, $R_3$, $R_4$, and $R_5$ are each independently selected from the group consisting of: hydrogen, deuterium, halogen, substituted or unsubstituted C1-C6 alkyl, amino, hydroxyl and nitro, wherein the "substituted" refers to being substituted by one or more substituents selected from the group consisting of: halogen, nitro, amino, and hydroxyl;

$R_6$ is selected from the group consisting of: hydrogen, deuterium, halogen, amino, and hydroxyl;

n is 0, 1, 2 or 3;

Q is selected from the group consisting of: C6-C10 aryl substituted or unsubstituted by one or more halogens, 6-10-membered heteroaryl containing 1-3 heteroatoms selected from N, O and S and substituted or unsubstituted by one or more halogens;

X is halogen.

2. The preparation method according to claim 1, wherein, in step 1), the catalyst is a substance or hydrate thereof selected from the group consisting of: copper (cuprous) iodide, copper (cuprous) chloride, copper (cuprous) bromide, copper sulphate, copper powder, copper (cuprous) oxide, copper (cuprous) hydroxide, copper (cuprous) acetate, copper citrate, copper methanesulfonate, copper fluoborate, basic copper carbonate, copper gluconate, copper (cuprous) tartrate, copper acetylacetonate, copper 8-hydroxyquinoline, copper (cuprous) thiocyanate, copper (cuprous) nitrate, copper (cuprous) cyanide, copper oxalate, copper phosphate, copper (cuprous) trifluoromethanesulfonate, copper formate, copper selenide, copper dichloro (1,10-phenanthroline), copper (1,10-phenanthroline) (trifluoromethyl) copper, CuTC, and combinations thereof.
3. The preparation method according to claim 1, wherein the compound of Formula I is selected from the group consisting of:
1
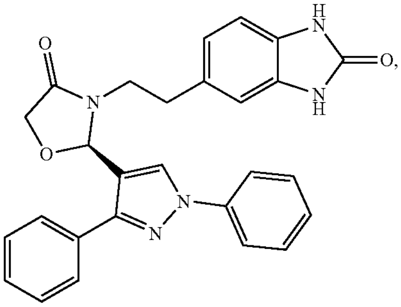
2
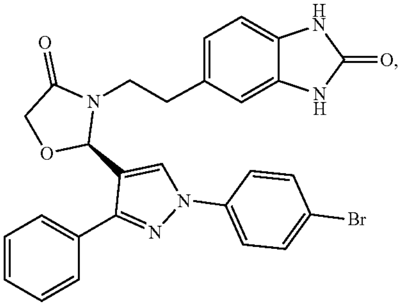
3
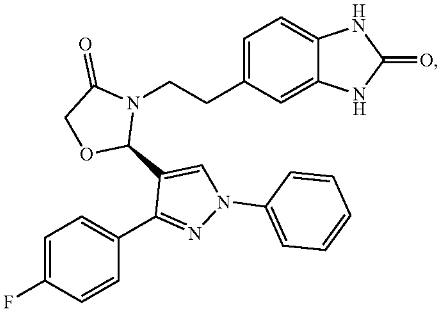
4
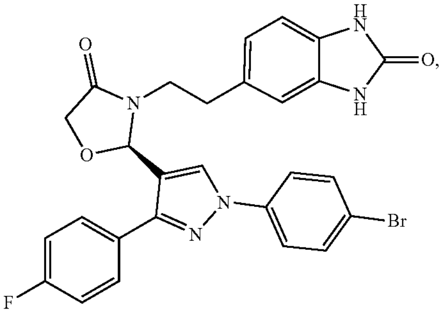
-continued
5
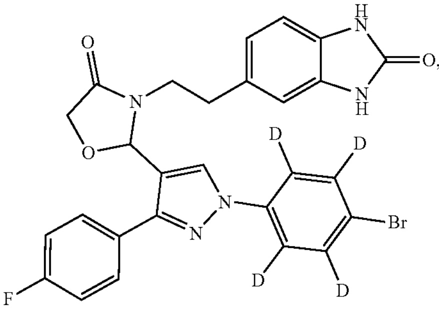
6
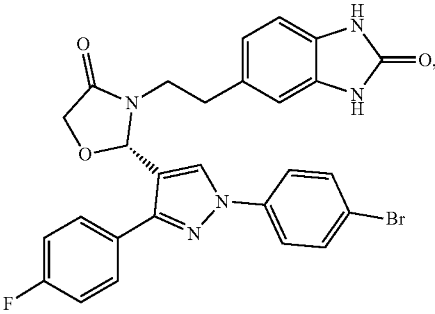
7
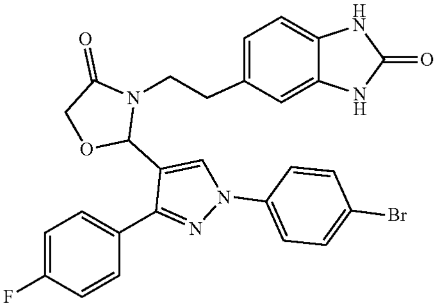
and
8
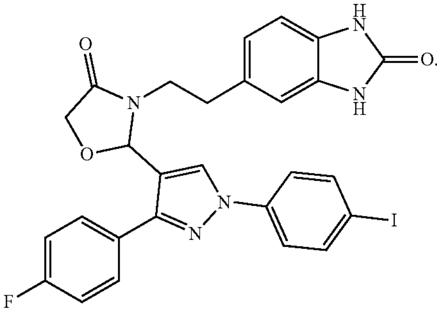
4. The preparation method according to claim 1, wherein, before step 1), the method further comprises the following step:

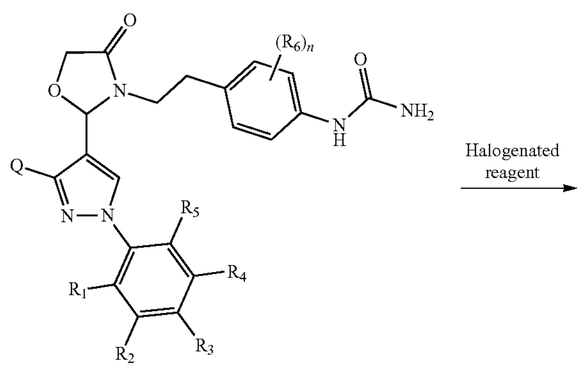

III

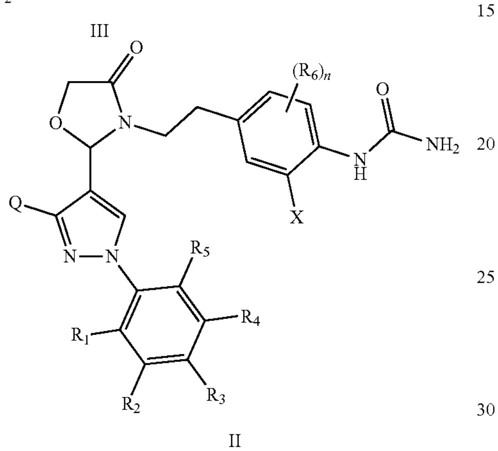

II 2) reacting a compound of formula III with a halogenated reagent to obtain a compound of formula II;

in the compound of formula III, $R_1$, $R_2$, $R_3$, $R_4$, $R_5$, $R_6$, n, X and Q are as defined in claim 1.

5. The preparation method according to claim 4, wherein in step 2), the halogenated reagent is selected from the group consisting of: N-iodosuccinimide (NIS), iodine, 1,3-diiodo-5,5-dimethylhydantoin, N-bromosuccinimide, bromine, 1,3-dibromo-5,5-dimethylhydantoin, chlorine, N-chlorosuccinimide, N-bromosuccinimide (NBS), and combinations thereof.

6. The preparation method according to claim 4, wherein, before step 2), the method further comprises the following step:

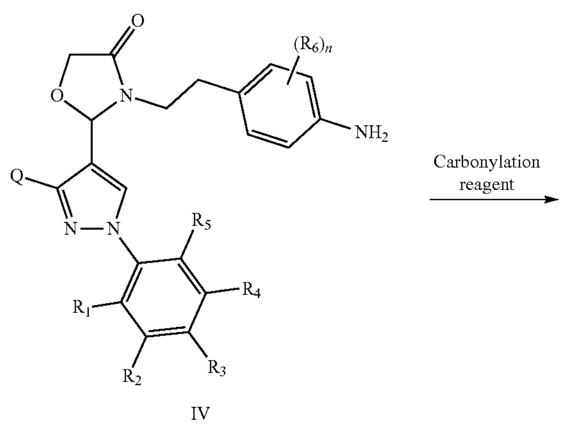

IV

-continued

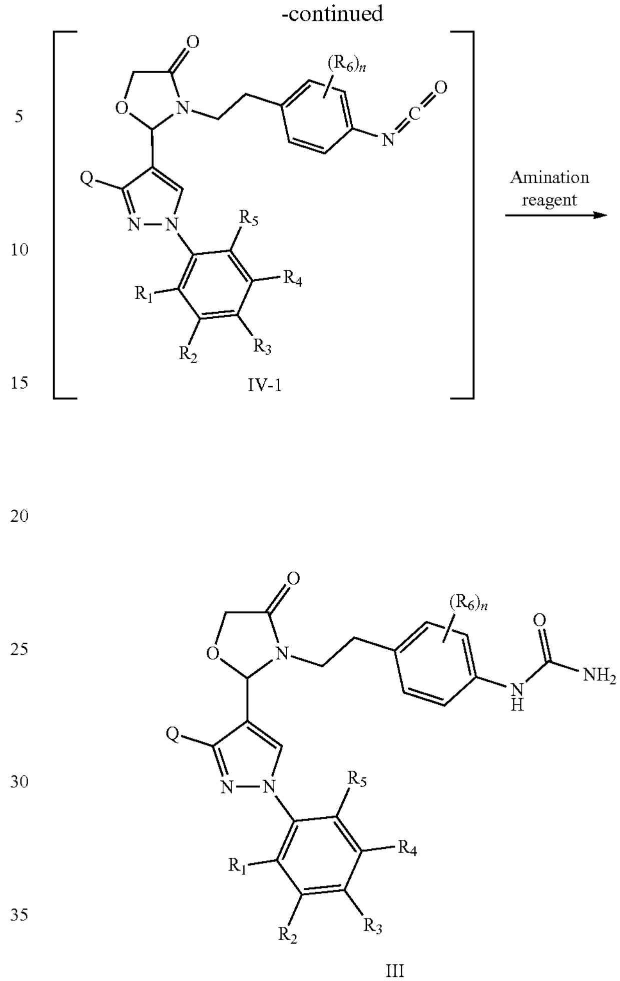

IV-1

III 3) reacting the compound of formula IV with a carbonylation reagent to obtain an isocyanate intermediate of formula IV-1;

4) reacting the isocyanate intermediate of formula IV-1 obtained from step 3) without separation with the amination reagent directly in the system to obtain the compound of formula III;

in the compound of formula IV and the isocyanate intermediate of formula IV-1, $R_1$, $R_2$, $R_3$, $R_4$, $R_5$, $R_6$, n and Q are as defined in claim 1.

7. The preparation method according to claim 6, wherein in step 3), the carbonylation reagent is selected from the group consisting of: triphosgene, CDI, potassium isocyanate, and combinations thereof; and/or in step 4), the amination reagent is selected from the group consisting of: ammonia, ammonia gas, an organic solution of ammonia, and combinations thereof.

8. An intermediate of formula II,

II

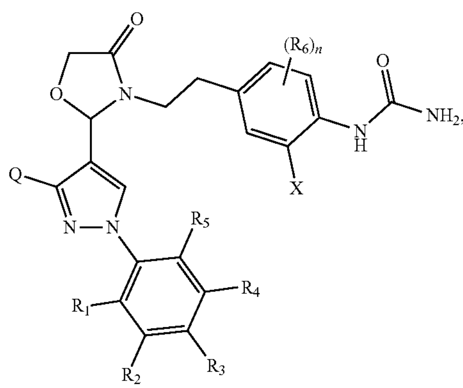

wherein, $R_1$, $R_2$, $R_3$, $R_4$, and $R_5$ are each independently selected from the group consisting of: hydrogen, deuterium, halogen, substituted or unsubstituted C1-C6 alkyl, amino, hydroxyl and nitro, wherein the "substituted" refers to being substituted by one or more substituents selected from the group consisting of: halogen, nitro, amino, and hydroxyl;

$R_6$ is selected from the group consisting of: hydrogen, deuterium, halogen, amino, and hydroxyl;

Q is selected from the group consisting of: C6-C10 aryl substituted or unsubstituted by one or more halogens, 6-10-membered heteroaryl containing 1-3 heteroatoms selected from N, O and S and substituted or unsubstituted by one or more halogens; and X is halogen.

9. An intermediate of formula III,

III

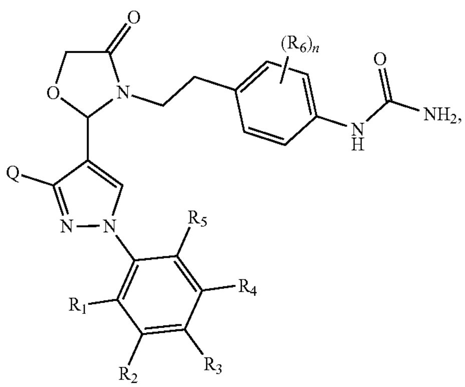

wherein, $R_1$, $R_2$, $R_3$, $R_4$, and $R_5$ are each independently selected from the group consisting of:

hydrogen, deuterium, halogen, substituted or unsubstituted C1-C6 alkyl, amino, hydroxyl and nitro, wherein the "substituted" refers to being substituted by one or more substituents selected from the group consisting of: halogen, nitro, amino, and hydroxyl;

$R_6$ is selected from the group consisting of: hydrogen, deuterium, halogen, amino, and hydroxyl;

Q is selected from the group consisting of: C6-C10 aryl substituted or unsubstituted by one or more halogens, 6-10-membered heteroaryl containing 1-3 heteroatoms selected from N, O and S and substituted or unsubstituted by one or more halogens; and X is halogen.

10. A method for preparing a compound of Formula I according to claim 1, or a pharmaceutically acceptable salt thereof, or a tautomer thereof, or a stereoisomer thereof, or a racemate thereof, the method comprising in the presence of a catalyst, subjecting an intermediate of formula II or an intermediate of Formula III to cyclization to obtain a compound of formula I:

II

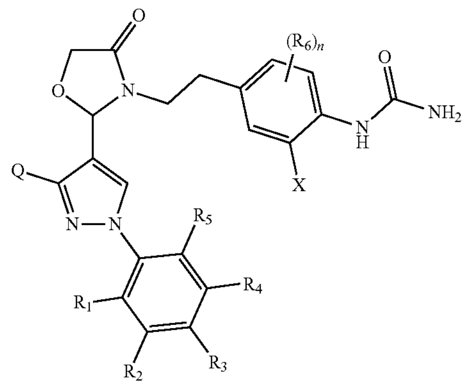

III

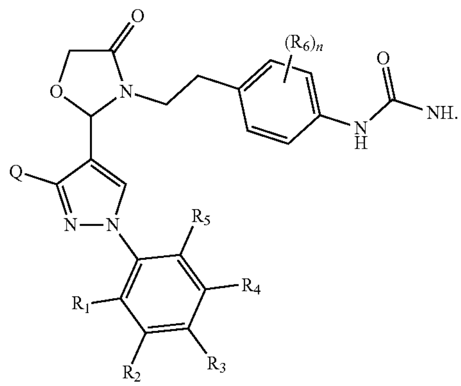

* * * * *